US010925529B2

(12) United States Patent
Helwa et al.

(10) Patent No.: US 10,925,529 B2
(45) Date of Patent: Feb. 23, 2021

(54) SYSTEM, METHOD, AND DEVICE FOR DETECTING POSTOPERATIVE COMPLICATIONS

(71) Applicant: NERv TECHNOLOGY INC., Waterloo (CA)

(72) Inventors: Youssef Helwa, Waterloo (CA); Amr Abdelgawad, Waterloo (CA); Mohammad Okasha, Waterloo (CA); Marc William Gibson, Kitchener (CA)

(73) Assignee: NERV TECHNOLOGY INC., Waterloo (CA)

(*) Notice: Subject to any disclaimer, the term of this patent is extended or adjusted under 35 U.S.C. 154(b) by 265 days.

(21) Appl. No.: 15/555,664

(22) PCT Filed: Mar. 7, 2016

(86) PCT No.: PCT/IB2016/051289
§ 371 (c)(1),
(2) Date: Sep. 5, 2017

(87) PCT Pub. No.: WO2016/142844
PCT Pub. Date: Sep. 15, 2016

(65) Prior Publication Data
US 2018/0042528 A1 Feb. 15, 2018

Related U.S. Application Data

(60) Provisional application No. 62/129,029, filed on Mar. 6, 2015, provisional application No. 62/138,466, filed
(Continued)

(51) Int. Cl.
A61B 5/1473 (2006.01)
A61B 5/00 (2006.01)
(Continued)

(52) U.S. Cl.
CPC .......... *A61B 5/1473* (2013.01); *A61B 5/0031* (2013.01); *A61B 5/1477* (2013.01);
(Continued)

(58) Field of Classification Search
None
See application file for complete search history.

(56) References Cited

U.S. PATENT DOCUMENTS

2008/0269582 A1 10/2008 Mansour et al.
2010/0204551 A1 8/2010 Roche
2013/0338770 A1 12/2013 Boyden et al.

FOREIGN PATENT DOCUMENTS

CA    2843008 A1    1/2013

OTHER PUBLICATIONS

International Search Report dated May 2, 2016 for International Patent Application No. PCT/IB2016/051289.
(Continued)

*Primary Examiner* — Marjan Fardanesh
(74) *Attorney, Agent, or Firm* — Perry + Currier Inc.

(57) ABSTRACT

Detecting postoperative complications in a patient uses a substrate made of biocompatible or biodegradable material. An adhesive layer adheres the substrate to patient tissue, surgical tool, or medical device. A biosensor at the substrate detects or measures an analyte in the patient's body. The biosensor may be on the surface of the substrate or within a microchannel in the substrate. A separation or isolation structure may be provided to separate or isolate the analyte from other analytes prior to the biosensor. A microcontroller is disposed on the substrate and connected to the biosensor and to a wireless communications interface also disposed on the substrate. The microcontroller measures a signal from the biosensor and may perform an analysis on the measured signal. Measured data or data resulting from the analysis is
(Continued)

transmitted through the wireless communications interface to a transdermal patch or other remote device for storage and display.

21 Claims, 22 Drawing Sheets

Related U.S. Application Data on Mar. 26, 2015, provisional application No. 62/216,764, filed on Sep. 10, 2015, provisional application No. 62/216,797, filed on Sep. 10, 2015.

(51) Int. Cl.
*A61B 5/1477* (2006.01)
*H02J 50/10* (2016.01)

(52) U.S. Cl.
CPC .......... *A61B 5/4848* (2013.01); *A61B 5/6833* (2013.01); *A61B 2560/0214* (2013.01); *A61B 2560/0219* (2013.01); *H02J 50/10* (2016.02)

(56) References Cited

OTHER PUBLICATIONS

Written Opinion dated May 2, 2016 for International Patent Application No. PCT/IB2016/051289.
International Preliminary Report on Patentability dated Sep. 12, 2017, by ISA, re PCT International Patent Application No. PCT/IB2016/051289.

SYSTEM, METHOD, AND DEVICE FOR DETECTING POSTOPERATIVE COMPLICATIONS

CROSS-REFERENCE TO RELATED APPLICATIONS

This application claims priority to U.S. 62/129,029, filed Mar. 6, 2015, U.S. 62/138,466, filed Mar. 26, 2015, U.S. 62/216,764, filed Sep. 10, 2015, and U.S. 62/216,797, filed Sep. 10, 2015. Each of these applications is incorporated herein by reference.

FIELD

The present disclosure relates to systems, methods, and devices for monitoring and detecting physiological and/or pathological changes within the body.

BACKGROUND

There are many kinds of surgical interventions for different disorders and diseases. Techniques include open, closed (such as biopsies) and minimally invasive techniques (such as laparoscopies) on patients in order to identify, diagnose and treat many pathological conditions or improve body functions. Surgical procedures include but are not limited to the following: abdominal, pelvic, cardiac, chest, neurological, dental, orthopedic, vascular, plastic, bariatric, gastrointestinal, genitourinary, reproductive, obstetrics and gynecologic. Surgical procedures can potentially save countless lives and improve health conditions. Nonetheless, with every surgical procedure comes a potential risk that a complication could happen.

Intra-operative and postoperative complications can severely affect an individual's health and can eventually initiate morbidity or even mortality. The complications that could develop are numerous and may be either general or specific to surgical intervention type and location. These include, but are not limited to: dangerous inflammation, leakage (anastomotic or injury), infection, shock (septic, hypovolemic, neurogenic), bleeding, tissue ischemia, organ injury, etc. Intra-operative and postoperative complications can occur for various reasons such as the body's natural reaction to certain changes in its system, place and type of surgery or due to accidental errors during the surgery. Some of these complications have extreme severity and can lead to permanent incurable health morbidities and/or mortality if not recognized and treated quickly.

Risk of serious intraoperative and postoperative complications is significant in certain forms of surgery including, but not limited to: abdominal surgery (especially if associated with adhesions, organ or mass removal), laparoscopy in different indications, cholecystectomy, anastomosis (organ or vascular; at micro and macro level), gastrointestinal resection and anastomosis, laparotomy for different disorders, cesarean section, and genitourinary surgeries. An example of a serious leak is anastomotic leakage that might arise from gastrointestinal anastomosis surgery where a segment of the gastrointestinal tract is removed and a reconnection is made to restore gastrointestinal continuity. This can cause morbidity and mortality and is one of the most feared complications if left undiagnosed or diagnosed too late. Other leakage might arise from vascular injury, organ injury, slipped ligature or ischemic changes. Risk to the patient is high, as abnormal fluid leakage or collection might contain or incubate bacterial elements as well as irritant constituents that can lead to peritonitis and/or septic shock. The same pathophysiological cascade can happen in other surgeries. An example would be abnormal fluid leak or collection into the chest, which could lead to mediastinitis, pleuritic effusion and pericarditis. In neurosurgery, it can cause hydrocephalus, hemorrhage and infection. In urological surgery, it can cause urinoma with consequent abscess formation, peritonitis and sepsis.

Minimally invasive surgeries are utilized by surgeons in different specialties for both diagnosing and management of many medical conditions. For example, laparoscopic procedures (e.g., abdominal, renal and pelvic surgeries) may have advantages over open surgical procedures. However, laparoscopic procedures have different settings that may lead to complications such as hemorrhage (internal or from port site), infection and organ injury (direct or electric through diathermy). Other minimally invasive surgery-related complications may include leakage of abnormal fluids such as gastric fluids, urine, bile or pus, which may cause critical morbidity and mortality. Fluid leakage or collection may occur as a consequence of organ damage, injury, slipped or improper stapling or stitching of major arteries, accidental cuts made by surgical instruments and/or infection. If left unattended or diagnosed late, those abnormally located fluids may lead to the deterioration of patients' health.

Technologies have been developed for the detection of postoperative complications. However, many of these technologies are costly and necessitate hospital readmission or frequent visits to healthcare providers for evaluation. Additionally, they lack high diagnostic efficacy, efficiency, specificity and sensitivity, the ability to provide real-time detection of postoperative complications and are time-consuming. Furthermore, many of these diagnostic technologies require highly equipped and timely reporting hospital services, skilled staff and teams from various specialties in order to ensure proper detection of postoperative complications within a harmless and safe time.

Methods for detecting postoperative complications include blood tests for different markers and parameters, use of different radiology models such as ultrasound waves, use of computerized axial tomography scans, magnetic resonance imaging and use of other electromagnetic energy to form scanned images of the internal structure of the human body.

Measuring biomarkers in patients' bodies has been widely used to predict post-surgical complications. One way of measuring biomarkers is characterizing analytes, such as proteins, in a patient's body. However, multiple analytes are often analyzed at the same time to accurately measure biomarkers. Furthermore, obtaining measurements of these proteins generally requires the biological fluid to be extracted from the body, via methods including blood sampling, peritoneal or fluid aspiration. In addition to extending the time needed to conduct a measurement, the extraction process may affect the composition of the biomarkers in the fluid.

The above techniques for detecting complications often have shortcomings. For example, detecting bacteria may require time for the bacteria to grow and multiply (for example, within the peritoneal cavity). In addition to that, a bacterial culture can take 48-72 hours to show the type of bacterial growth, if any. By the time proliferation occurs, it may be too late to avoid serious complications affecting the patient, such as sepsis, irreversible septic shock, or death. Capacitance-detecting strain or tension sensors may be designed to attach to the point of maximum leak incidence (for example, the area of anastomosis). This placement may cause difficulty for physicians and surgeons in securing proper placement (for example, when using laparoscopic tools). Further, leakage may occur in an unexpected region away from the positioning of the sensor. Gas pressure monitoring sensors may encounter the issue of providing a sufficient current source for accurate detection and communication. Some methods that measure electrolyte resistance may include invasive probing, with electrodes physically wired to an external system. Such a system may be impractical and inconvenient for continuous and effective postoperative monitoring. Additionally, scanning techniques such as computerized axial tomography scans, magnetic resonance imaging, ultrasound scan, and other imaging techniques can provide inaccurate information about the type of complication (for example, the type of fluid collection). A lack of specificity in the images produced may not be sufficient for early detection. Additionally, such techniques may not provide information about the complications in real-time, thereby delaying the detection process.

SUMMARY

According to one aspect of the present invention, a device for detecting postoperative complications in a patient includes a substrate made of biocompatible or biodegradable material and an adhesive layer at a surface of the substrate. The adhesive layer is configured to adhere the substrate to a carrier. The device further includes at least one biosensor disposed at the substrate. The at least one biosensor is configured to detect or measure at least one analyte in a body of the patient. The device further includes a wireless communications interface disposed on the substrate and a microcontroller disposed on the substrate. The microcontroller is connected to the at least one biosensor and the wireless communications interface. The microcontroller is configured to measure at least one signal from the at least one biosensor, perform an analysis on the at least one measured signal, and transmit data from the analysis through the wireless communications interface to a remote device. The device further includes a power source for powering the wireless communications interface and the microcontroller.

The at least one biosensor can include a pair of ion-selective electrodes.

The pair of ion-selective electrodes can be disposed on a top surface of the substrate.

The device can further include at least one microfluidic channel in the substrate. The at least one biosensor can be disposed within the at least one microfluidic channel.

The at least one microfluidic channel can include an electrically charged wall.

The electrically charged wall can be positively charged.

The electrically charged wall can be negatively charged.

The device can further include analyte substrates disposed within the at least one microfluidic channel. The analyte substrates can at least partially obstruct flow through the microfluidic and be consumable by at least one analyte.

The analyte substrates can be embedded in a polymer structure.

The analysis can be configured to relate flow rate through the microfluidic channel to concentration of the at least one analyte.

One or more porous polymer structures can be disposed in the microfluidic channel. The one or more porous polymer structures can define one or more pore sizes for separating or isolating different analytes.

The microcontroller can be configured to measure voltage, current, resistance, resistivity, conductivity, circuit frequency, time, electrical induction, capacitance, or a combination of such.

The device can further include conductive material disposed in the at least one microfluidic channel and connected to the power source, and an aptamer, antibody, or combination of such in the at least one microfluidic channel.

The aptamer, antibody, or combination of such can be embedded directly into the at least one microfluidic channel.

The aptamer, antibody, or combination of such can be embedded in the conductive material.

The aptamer, antibody, or combination of such can be disposed on the surface of the conductive material.

The device can further include a pair of electrodes spanning the at least one microfluidic channel. The microcontroller can be configured to detect or measure binding of an analyte to the aptamer, antibody, or a combination using the pair of electrodes.

The conductive material can include a nanoparticle sheet.

The conductive material can include a polymer, hydrogel, or microgel.

The device can further include at least one further biosensor disposed on the substrate outside the at least one microfluidic channel.

The least one biosensor can include an aptamer, antibody, or combination of such.

The adhesive layer can include a bioadhesive configured to adhere to internal tissue of the patient.

The carrier can be a surgical instrument.

The carrier can be a medical device.

The biosensor can be configured for electrolytic zero-current fluid detection.

The power source can include a battery.

The power source can include an inductive coil for receiving power from a remote device outside the body.

The wireless communications interface can include a radio-frequency identification device.

The remote device can include a transdermal patch.

The remote device can include a smartphone or tablet computer.

According to another aspect of the present invention, a system for detecting postoperative complications in a patient includes a transdermal patch configured to adhere to skin of a patient, the transdermal patch including a wireless communications interface. The system further includes a substrate made of biocompatible or biodegradable material and an adhesive layer at a surface of the substrate. The adhesive layer has a bioadhesive configured to adhere the substrate to internal tissue of the patient. The system further includes at least one biosensor disposed at the substrate, the at least one biosensor configured to detect or measure at least one analyte in a body of the patient. The system further includes a wireless communications interface disposed on the substrate and a microcontroller disposed on the substrate. The microcontroller is connected to the at least one biosensor and the wireless communications interface. The microcontroller is configured to measure at least one signal from the at least one biosensor and transmit measured data through the wireless communications interface disposed on the substrate to the wireless communications interface of the transdermal patch. The system further includes a power source disposed on the substrate for powering the wireless communications interface disposed on the substrate and the microcontroller.

The transdermal patch can further include a processor configured to perform an analysis on the measured data.

According to another aspect of the present invention, a method for detecting postoperative complications in a patient includes powering a wireless communications interface and a microcontroller of a biochip when a substrate of the biochip made of biocompatible or biodegradable material is adhered to a carrier, at least one biosensor disposed at the substrate detecting or measuring at least one analyte in a body of the patient, measuring at least one signal from the at least one biosensor, performing an analysis on the at least one measured signal, transmitting data from the analysis through the wireless communications interface to a remote device, and outputting the data from the analysis.

The method can further include at least partially obstructing flow through at least one microfluidic channel in the substrate using analyte substrates disposed within the at least one microfluidic channel and being consumable by the at least one analyte, and relating flow rate through the at least one microfluidic channel to concentration of the at least one analyte.

The method can further include detecting or measuring binding of an analyte to a aptamer, antibody, or a combination of such disposed in at least one microfluidic channel in the substrate using a pair of electrodes spanning the at least one microfluidic channel.

The method can further include isolating or separating analytes at the substrate prior to the at least one biosensor detecting or measuring the at least one analyte in the body of the patient.

The isolating or separating can be performed using an electrically charged wall of at least one microfluidic channel in the substrate.

The isolating or separating can be performed using one or more porous polymer structures disposed in at least one microfluidic channel in the substrate.

BRIEF DESCRIPTION OF THE DRAWINGS

The drawings illustrate, by way of example only, embodiments of the present disclosure.

DETAILED DESCRIPTION

Figure 1:
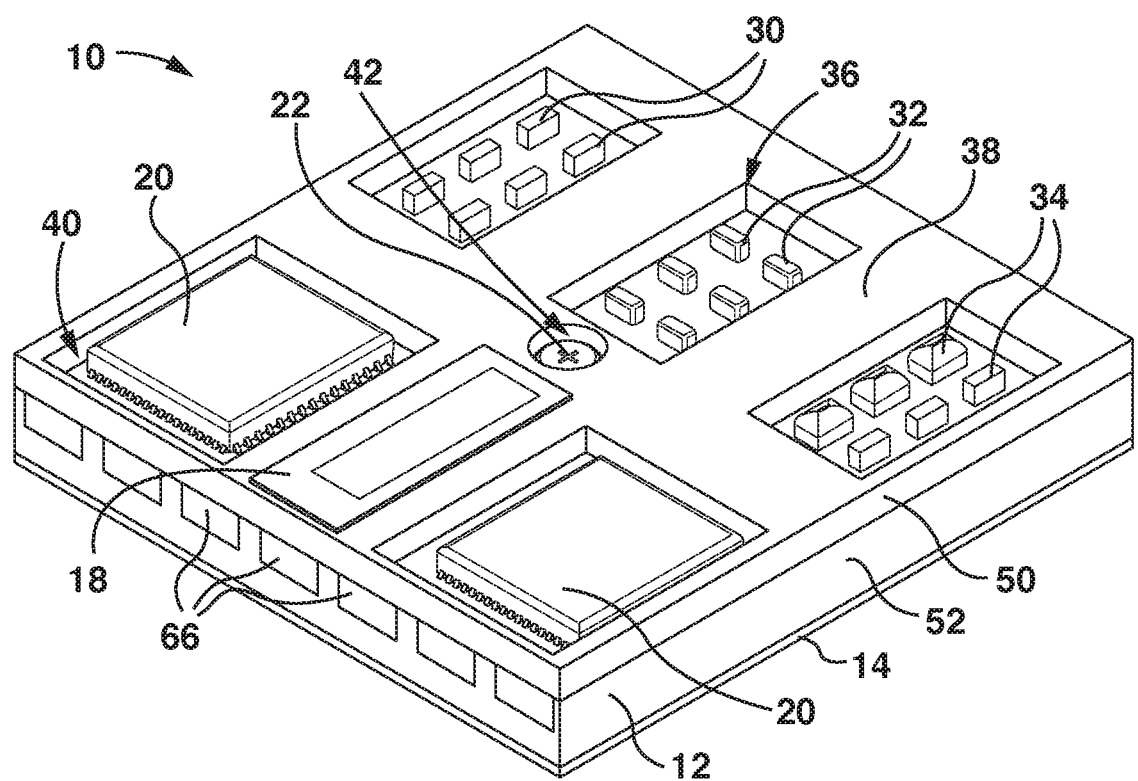
FIG. 1 is a perspective view of a biochip.

The present invention relates to devices, systems, and methods capable of monitoring a patient's (e.g., human or animal) health after a surgical operation. The invention serves to assist in detecting postoperative complications including, but not limited to, leakage (anastomotic, vascular or organ perforation such as urine, bile, gastric fluids), dangerous inflammation, bacterial growth, infection, internal bleeding, ischemic changes, changes in pH, and changes in glucose level. The invention can be made mobile, small, cost-effective, predictive, accurate, and can provide real-time data about different patient health parameters.

The term "analyte" as used herein refers to substances, chemical constituents of a biological fluid (e.g., hydronium and hydroxide ions, salt ions, biological acids and bases such as sodium, calcium, magnesium, nitrates, lactic acid etc.), biological substances (e.g., proteins, bacterial protein, inflammatory proteins, carbohydrates or enzymes such as tumor necrosis factor alpha, deoxyribonucleic acid or DNA, interleukin-1 beta, lipids, interleukin-8, interleukin-12, ADAM 17, glucose, lactase etc.) and organisms (e.g., cellular organisms, bacteria, viruses, etc.) that can be analyzed. Analytes include substances that occur naturally in the body as well as synthetic substances.

The term "bodily fluid" or "biological fluid" as used herein refers to fluids originating from a human or animal body, fluids that are excreted or secreted by a body (e.g., human blood, gastric juice, peritoneal fluid, amniotic fluid, urine, bile, sebum, etc.), and similar fluids. Fluids may be liquids, gasses, or a combination.

The terms "microchannel" and "microfluidic channel" as used herein refer to a small-scale physical structure that defines a passage for fluids that can enable control and/or manipulation of the flow. Microchannels can be made by several methods including, but not limited to, silica-based methods, photolithography, electron beam lithography, 3-D printing, mechanical etching, laser etching, wet chemical etching, micro-injection modeling, and micro-embossing. Materials that can be used to produce microchannels include, but are not limited to, silicon, quartz, glass, silicon rubber, and polymers (plastic).

The term "biomarker" as used herein refers to a substance or state that is detectable or measurable and that is indicative of some phenomenon such as disease, infection, or environmental exposure. Biomarkers include, but are not limited to, cells, molecules, genes, gene products, enzymes, hormones, proteins, antibodies, bacteria, glucose, and pH. Biomarkers may be related to or indicative of biological parameters (or "bio-parameters") such as bleeding, bacterial activity, inflammatory protein, and others as discussed elsewhere herein.

The term "aptamer" as used herein refers to any material (e.g., oligonucleotides, peptides, antibodies, metals, ionic salts, etc.) that binds to a specific molecule, analyte, or biomarker. Oligonucleotide aptamers include but are not limited to DNA, ribonucleic acid (RNA), and xeno nucleic acid (XNA). Peptide aptamers include, but are not limited, to antibodies and short unstructured peptides.

Figure 2:
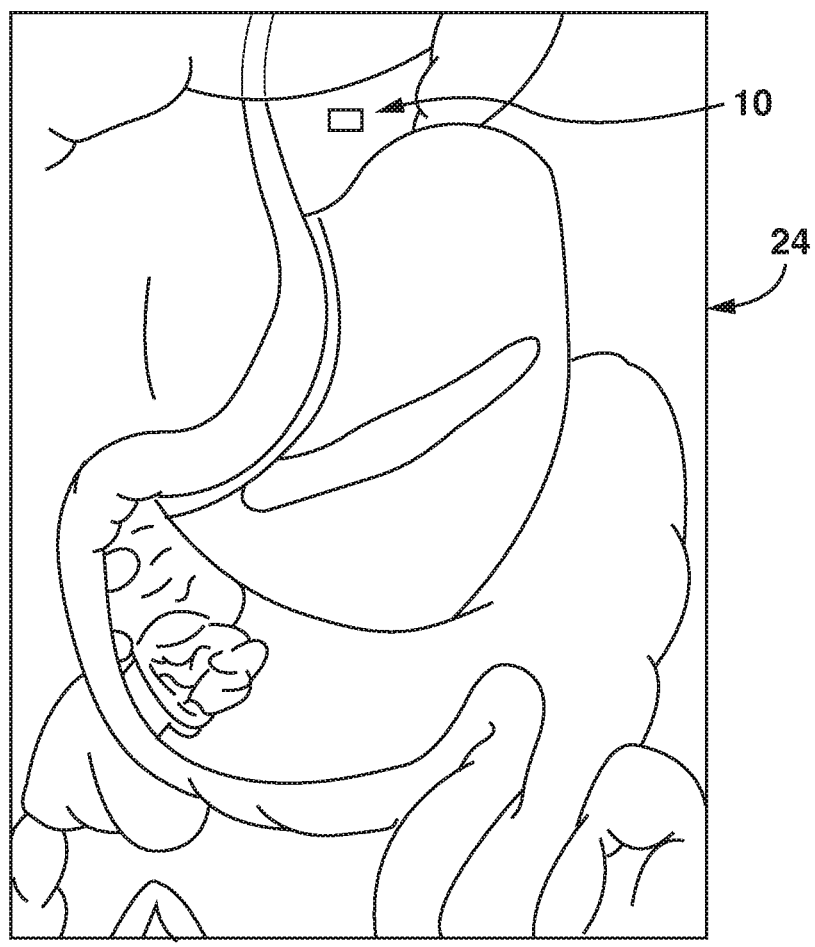
FIG. 2 is a diagram of the biochip implanted in the body of a patient.
Figure 3:
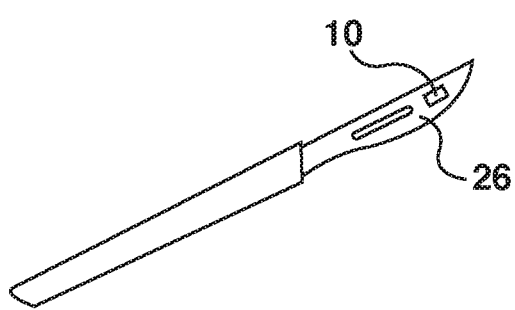
FIG. 3 is a diagram of the biochip attached to a surgeon's instrument.
Figure 22:
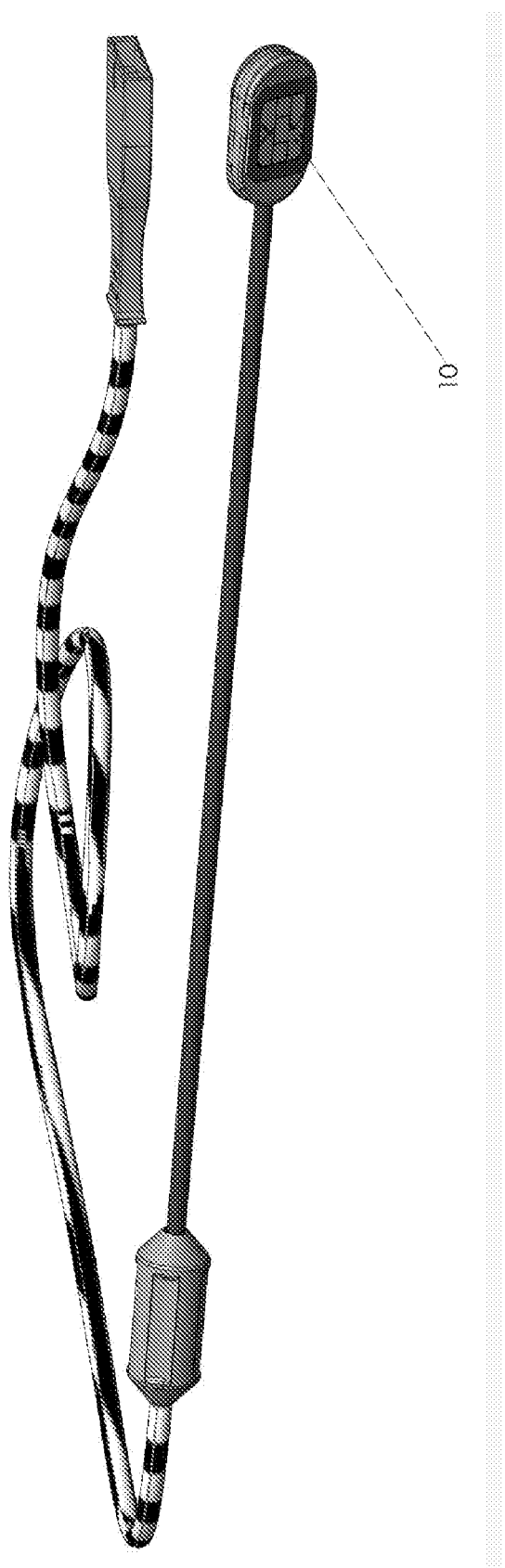
FIG. 22 is a diagram of the biochip attached to a medical device.

FIG. 1 shows a biochip 10 according to an embodiment of the present invention. The biochip 10 includes a substrate 12, adhesive layer 14, at least one biosensor, a wireless communications interface 18, a microcontroller 20, and a power source 22. As will be discussed below, the biochip 10 is configured to detect postoperative complications and can be configured to adhere to internal tissue of the patient at a point adjacent to the location of a surgical site, to a surgical instrument used by a surgeon during an operation, to a medical device implanted into the patient, or to a medical device used to monitor the patient following surgery. Postoperative complications may be detected by detection of various fluids (liquids or gasses). The biochip 10 can be made small enough to fit through openings made by surgical instruments (e.g., laparoscopic tools). FIG. 2 shows the biochip 10 adhered to the wall of the peritoneal cavity 24. FIG. 3 shows the biochip 10 adhered to a scalpel blade 26. FIG. 22 shows the biochip 10 adhered to a fetal scalp electrode.

The substrate 12 provides a main physical layer that supports the physical structure of the biochip 10 and provides a structural framework for functionality of the biochip 10. The substrate 12 is made of biocompatible or biodegradable material. Examples of suitable substrate materials include silicon, titanium, gold, silver, glass, quartz, polyimide, parylene polyimide, Poly-L-lactic acid (PLLA), and polydimethylsiloxane (PDMS), and selection of a specific material may depend on specific implementation requirements. Other suitable materials may be used. The substrate 12 can take the shape of a planar rectangle, as shown, or can take other shapes. The substrate 12 can be flexible to conform to the shape of the carrier to which it is adhered.

The adhesive layer 14 is provided at a surface of the substrate 12, such as the bottom side of the substrate 12, as shown. The adhesive layer 14 is configured to adhere to the substrate 12, and thus the biochip 10, to a carrier, such as patient tissue (e.g., organ surface or the wall of the peritoneal cavity), a surgeon's instrument (e.g., a scalpel), an implantable medical device, or to a medical device that can be used to monitor the patient following surgery (e.g., peritoneal drains). The adhesive layer 14 can be a separate layer of material bonded to the substrate 12 or can be a layer integral with the substrate 12 of the biochip 10. Examples of bioadhesives usable for a separate adhesive layer 14 when attaching the biochip 10 to patient tissue include, but are not limited to, sugars, proteins, polymeric gels, and similar. When attaching the biochip to a surgical instrument or medical device, any suitable medical-grade adhesive can be used for the adhesive layer 14.

Biosensors are disposed at the substrate 12. Shown in FIG. 1 are various biosensors 30, 32, 34 disposed in trenches 36 in a top surface 38 of the substrate 12. Various types and positions of biosensors are contemplated, as will be discussed in greater detail below, including biosensors within microfluidic channels (or microchannels). The biosensors are configured to detect or measure one or more analyte, biomarker or bio-parameter in a bodily fluid, where the one or more analyte, bio-parameter or biomarker is indicative of one or more postoperative complications.

The wireless communications interface 18 is disposed on the substrate 12, for example, at the top surface 38 of the substrate 12. The wireless communications interface 18 includes an antenna and can further include support circuitry. The wireless communications interface 18 is configured to wirelessly communicate data through any intervening body tissue or medical device to a remote device, such as a transdermal patch, smartphone, tablet computer, or similar device. Bluetooth or Bluetooth Low Energy (BLE) may be used.

The one or more microcontrollers 20 are disposed on the substrate 12, for example, within one or more trenches 40 in the substrate 12. The microcontroller 20 is configured to detect or measure at least one signal from the biosensors and perform an analysis on the measured signal. The microcontroller 20 can include a voltmeter, ammeter, timer, ohmmeter, spectrum analyzer, induction meter (inductometer), or a capacitance meter (capacimeter) to perform measurements to obtain electrical, spectral, or other characteristics/properties. The microcontroller 20 can execute one or more programs to perform the analysis. The microcontroller 20 is further configured to transmit data obtained from the analysis through the wireless communications interface 18 to the remote device. The microcontroller 20 may include integrated memory or a separate memory chip may be provided as disposed on the substrate 12. The memory is configured to store the one or more programs and any reference data needed for measurement and analysis.

The analysis can take different forms depending on the biomarkers being detected/measured and the parameters being examined. For example, concerning inflammatory proteins and bacterial activity, the analysis is configured to take a baseline reading indicating levels of the relevant biomarkers as soon as the biochip 10 is implanted. Subsequently, the analysis determines the rate of change of the biomarkers (e.g., by computing a gradient or slope) to identify how the body is responding to the surgery. It is expected that the level of inflammatory biomarkers will peak just after the surgery because the body was just exposed to potential pathogens. However, it is also expected that the levels of these biomarkers will drop in the hours following surgery. The analysis can thus be configured to periodically compute and output the rate of change during the hours or days following surgery, so that the rate of change can be monitored for any indication of a complication.

In another example of an analysis, a microfluidic channel is used to measure a base reading of local pH. Then, ion-sensitive electrodes are used to measure a rate of change to determine the pH inside the body. The analysis is configured to compute this pH using the base reading and the rate of change.

The power source 22 is disposed on the substrate, for example, in a trench 42. The power source 22 can provide power to the wireless communications interface 18, the microcontroller 20, biosensors placed on the surface to the biochip, and biosensors placed in the microchannels. The power source 22 can include one or more of a single-use battery, a rechargeable battery, an inductive coil for receiving power from a remote device outside the patient's body, and an energy harvesting device for capturing kinetic energy, thermal energy, electromagnetic energy, or similar. When the power source 22 includes an inductive coil, the same remote device that communicates data with the biochip 10 can be configured to provide electrical power to the power source 22 via induction. The wireless communications interface 18 and power source 22 may together form a radio-frequency identification device (RFID). Alternatively or additionally, a separate and distinct remote device can be used to provide inductive power to the power source 22.

The wireless communications interface 18, microcontroller 20, power source 22, and biosensors are mutually connected via wires, traces, and/or interconnects, which can be made from metals (e.g., titanium, gold, platinum, etc.), semiconductor (e.g., silicon, gallium arsenide, etc.), electrically conductive polymer (e.g., polypyrrole, polyanilines, etc.), or similar.

To prevent bodily fluids and other materials from affecting operation of the biochip 10, the wireless communications interface 18, microcontroller 20, and power source 22 can be coated or covered in biocompatible and/or biodegradable material. Alternatively or additionally, the wireless communications interface 18, microcontroller 20, and power source 22 can be encapsulated in an encapsulant, which can include biocompatible and/or biodegradable materials, such as polymers, a metal casing, ceramic, or a combination of such.

In general operation, the biochip 10 is adhered to the carrier by use of the adhesive layer 14. The one or more biosensors at the biochip 10 measure signals from one or more analytes in the vicinity of the biochip 10. The measured signals are digitized by the microcontroller 20 and may be stored temporarily in memory at the biochip 10 or wirelessly transmitted to a transdermal patch or other remote device for storage and/or display. The microcontroller 20 performs one or more analyses on the digitized measured signals and generates data, which may also be stored temporarily in memory at the biochip 10 or wirelessly transmitted to the transdermal patch or other remote device for storage and/or display. Under the control of the microcontroller 20, the wireless communications interface 18 transmits the data to a remote device brought into the effective range of the wireless communications interface 18.

In various embodiments, one or more of the biosensors 30, 32, 34 include one or more electrochemical sensors that include one or more reference electrodes and one or more sensing electrodes. The reference electrodes, sensing electrodes, conductive wires, traces, and/or interconnects, and microcontroller 20 are all adhered to the top surface 38 to form an electrochemical system. When in-vivo bodily fluid comes into contact with the electrochemical system, the microcontroller 20 measures a potential (voltage) between the electrodes using a difference in work functions and a hydrated ionic gel layer between the electrodes. Measured potentials are then stored as measured data in memory of the biochip 10. In some embodiments, the electrodes are connected to an open circuit that is closed when exposed to ionic biological fluids, resulting in a signal that can be measured by the microcontroller 20. The microcontroller 20 performs an analysis on the measured data. Resulting data is transmitted via the wireless communications interface 18 to a remote device (e.g., a transdermal patch) for communication to a display device or other remote device for presentation to relevant individuals, such as a physician, veterinarian, caregiver, or the patient.

In various embodiments, one or more of the biosensors 30, 32, 34 are configured to measure a potential difference between two ion-selective electrodes to detect changes in pH, for example, in a patient's abdominal region. A measured voltage difference may indicate a rise/drop in pH inside the abdominal region, which may provide an indication of a biological fluid being released into the body, local bacteria metabolism, dangerous inflammation, wound healing, or ischemic development in the region. In some embodiments, a pH-measuring biosensor 30, 32, 34 is provided with a biodegradable polymer which degrades at low pH levels. The biodegradable polymer is disposed over an electrode and degradation of the material exposes the electrode, which completes (or increases current flow in) a circuit that is monitored by the microcontroller 20. In other embodiments, a pH-measuring biosensor 30, 32, 34 includes two electrodes and is configured to detect changes in pH by detecting variance in current transmitted between the two electrodes. Variance in such current can be attributed to the charging of ionic species present in the fluid between the electrodes.

Figure 4:
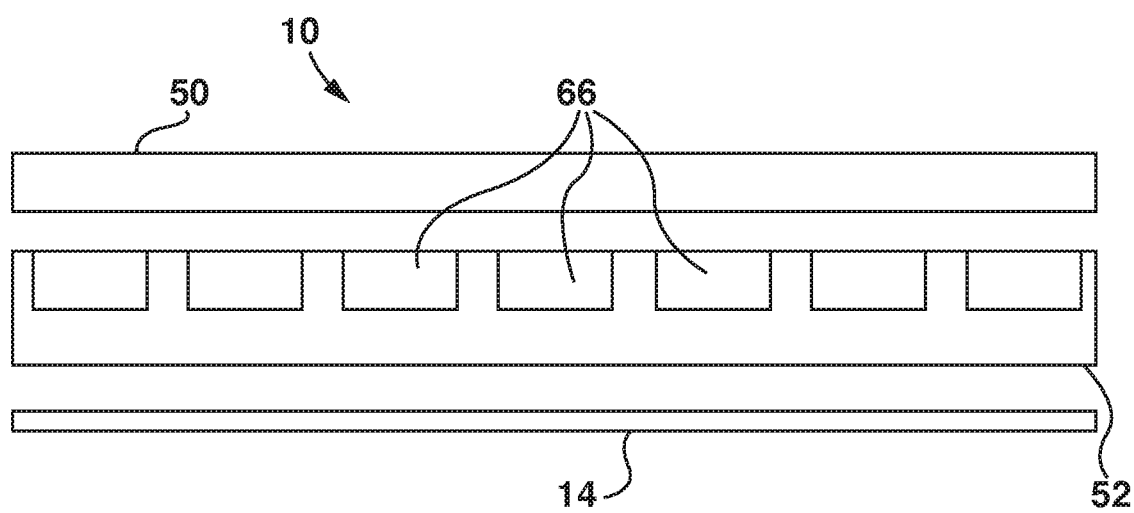
FIG. 4 is a side exploded view of the biochip.

In this embodiment, as shown in FIG. 4, the biochip 10 includes a top layer 50 that defines the top surface 38. The top layer 50 is disposed over a channel layer 52. The top layer 50 and channel layer 52 together form the substrate 12. The wireless communications interface 18, microcontroller 20, power source 22, and surface biosensors 30, 32, 34 are provided in the top layer 50, and microchannels can be provided between the top layer 50 and the channel layer 52, as discussed below.

Figure 5:
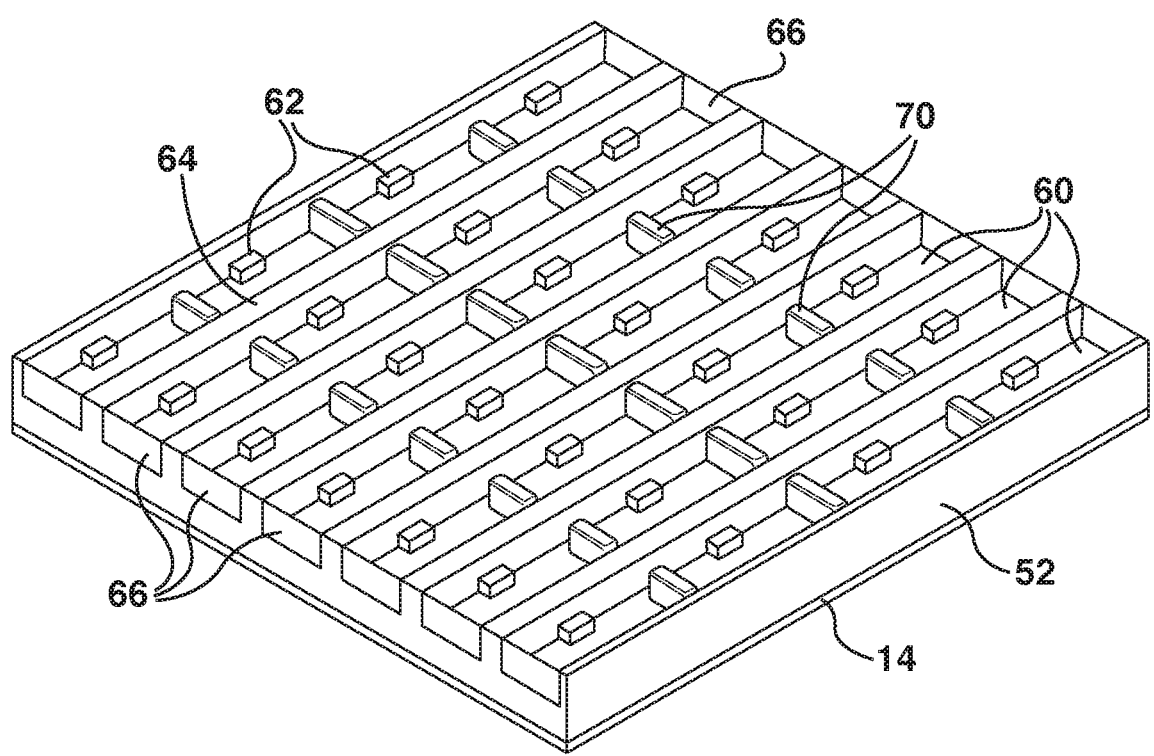
FIG. 5 is a perspective view of a channel layer of the biochip.

As shown in FIG. 5, in this embodiment, the biochip 10 includes one or more internal microfluidic channels 60 extending through the substrate 12, as defined by the channel layer 52 and enclosed by the top layer 50. At least one biosensor is disposed within the microfluidic channels 60. One or more separation/isolation structures may be disposed in the microfluidic channels 60 to enable selection of analytes/biomarkers of interest. In this embodiment, a plurality of microfluidic channels 60 are arranged parallel to each other. Each microfluidic channel 60 is an enclosed channel with two open ends and is configured to allow the flow of fluid. Generally, the microfluidic channels 60 can be configured to allow fluid flow, analysis, preparation, filtration, separation, mixing, sensing and storing.

The microfluidic channels 60 can include two or more pairs of ion-selective electrodes 62, 64 and/or various polymer structures 70 disposed therein. The electrode pairs 62, 64 and/or polymer structures 70 are configured to operate as one or more biosensors, with electrode pairs 62, 64 measuring properties of analytes and with polymer structures 70 providing various functions such as filtering analytes, binding analytes, bearing analyte substrates.

A microfluidic channel 60 can be pre-filled with synthetic fluid that allows for calibration of the electrodes 62, 64 after deployment (e.g., inside the abdominal cavity). An example of this application is a pH sensor requiring an initial calibration by utilizing one or more predefined buffers. The buffers can be prepared and stored at the biochip 10 before the biochip 10 is utilized in a clinical environment. The microcontroller 20 can be configured to re-calibrate measured data using the buffer that has been pre-stored in the microfluidic channel 60.

The ion-selective electrodes 62, 64 (and as used in the surface biosensors 30, 32, 34) can include at least one counter electrode (e.g., electrode 62) and one working electrode (e.g., electrode 64). The electrodes may include silver, gold, titanium, platinum, graphene, graphite, silicon, carbon nanotubes, polypyrrole, polyanilines, or another suitable material. A third reference electrode may be used. The electrodes can be coated (surface modified) with DNA, lipid, enzymatic, metallic, antibody or peptide aptamers, which allows for selectivity in terms of the biomarkers that are being analyzed. Polymeric electrodes can be modified by embedding one or more aptamers into a polymeric network allowing sensitivity and binding of the biomarkers into the network.

The surface area of biosensor electrodes, whether in microfluidic channels 60 or on the top surface 38, can be designed for a desired response. For example, larger electrode surface area in contact with ions in the bodily fluid is contemplated to allow for a longer or a more sensitive signal response.

The polymer structures 70 may be composed of material such as polyacrylamides, polymacon, polyethylene oxide, polyAMPS™, polyvinylpyrrolidone, alumina or another suitable porous materials. Various polymer structures will be discussed in detail below.

In this embodiment, the microfluidic channels 60 are provided with outer membranes 66 positioned to cover the open ends of the microfluidic channels 60. The membranes 66 are configured to allow the passage of biological fluids (e.g., water, blood, peritoneal fluid, bile fluid, gastric juice, etc.) into and through the microfluidic channels 60. The microfluidic channels 60 can be configured to be openable using various techniques of controlling the membranes 66. The membranes 66 can be thermally or electrically actuated. Electrical actuation can be controlled by the microcontroller 20. The membranes 66 can be configured to undergo biological degradation or electrical degradation via an applied voltage. The membranes 66 can be made out of biodegradable materials that degrade after a specified period. The time at which the degradation happens can be controlled by modifying a polymeric membrane 66 thickness, material, or another chemical or physical property. The membranes 66 can be synthesized from porous materials that can filter biological fluids or modify the biological fluid that will be analyzed. The membranes 66 can be fabricated out of different polymers, such as hydrogels (poly(L-lactide), acrylic, etc.), or metals, such as gold or platinum.

In other embodiments, the biochip 10 incorporates sheets of nanomaterials, such as graphene, carbon nanotubes, gold etc. Such sheets can have different components (e.g., linkers or aptamers) attached to them (e.g., surface modified) enabling the sensing of different analytes. These components include DNA aptamers, peptide aptamers, enzymes, catalysts, etc. Such analytes include different inflammatory markers, immunological markers, and similar, as discussed elsewhere herein. In various embodiments, one or more sheets of nanomaterials are placed directly on top of the biochip 10, such as on the top surface 38, to be in direct contact with biological fluids. In various embodiments, one or more sheets of nanomaterials are placed in one or more microfluidic channels for analysis of controlled samples of biological fluids. The placement of sheets of nanomaterials in specific implementations depends on the analyte being sensed and the aptamer being used.

Figure 6:
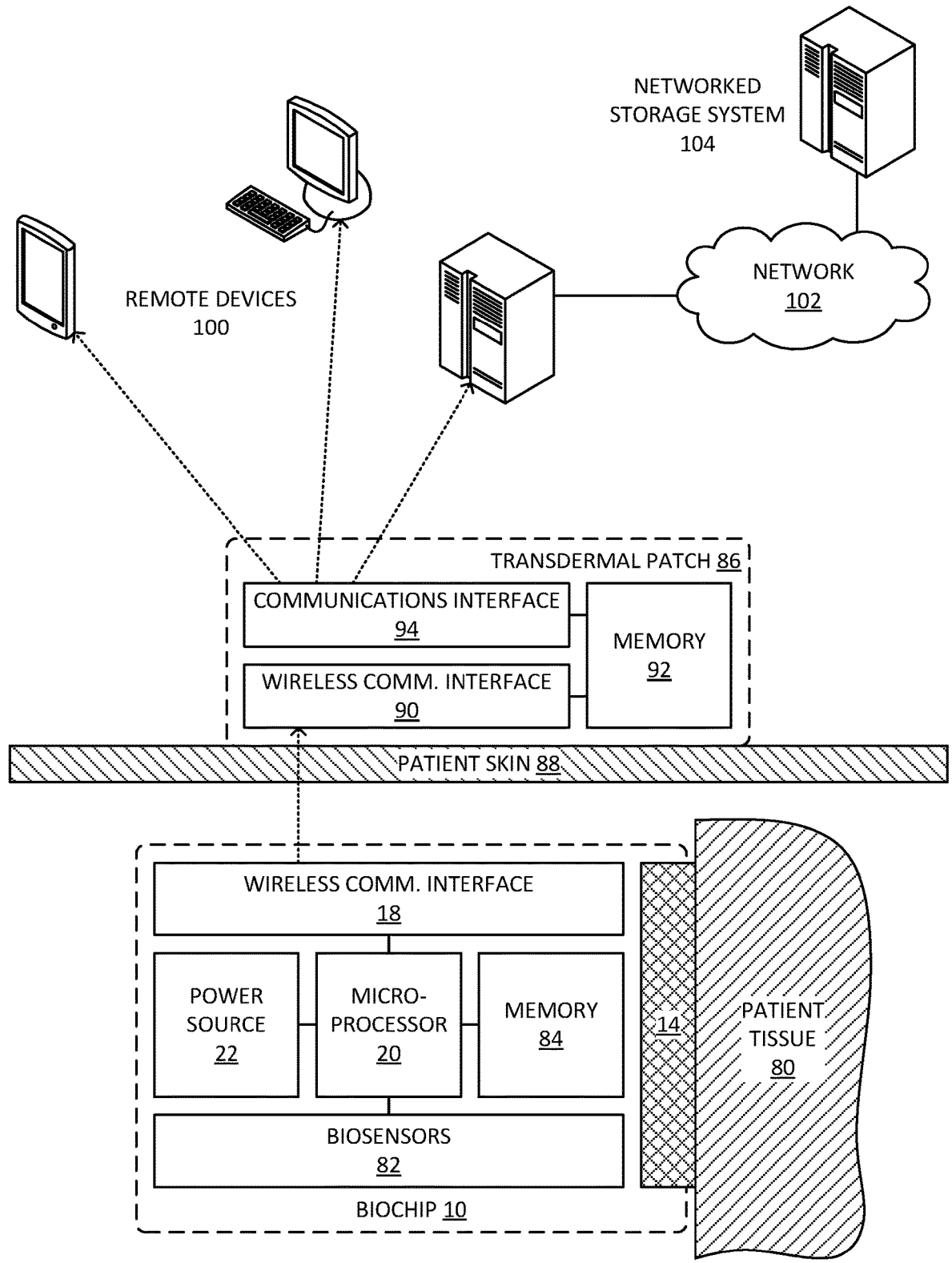
FIG. 6 is a block diagram of the biochip, a transdermal patch, and other remote devices.

FIG. 6 shows the biochip 10 implanted within a patient's body. As shown, the adhesive layer 14 of the biochip 10 bonds to patient tissue 80. Signals are measured by one or more biosensors 82 of the biochip 10 and converted into data by the microcontroller 20. The biosensors 82 include any of the biosensors discussed herein, implemented with or without isolation/separation structures discussed herein. The data is stored in memory 84 of the biochip 10. The wireless communications interface 18 communicates data in the memory 84 to a remote device outside the patient's body, such as a transdermal patch 86 adhered to the patient's skin 88 near the location of the biochip 10 in the body. The transdermal patch 86 includes a wireless communications interface 90 for communicating with the wireless communications interface 18 of the biochip 10. The transdermal patch 86 further includes memory 92 for storing data received from the biochip 10. The transdermal patch 86 can further include a wired or wireless communications interface 94 for transmitting the stored data to one or more other remote devices 100, including but not limited to smartphones, tablet computers, desktop computers, servers, or similar. Remote devices 100 may be operated by any one or more of the patient, a family member, a nurse, a caregiver, a physician, a veterinarian, a surgeon, a medical facility, or another individual or organization concerned with the welfare of the patient.

The communications interface 94 can be different from the wireless communications interface 90 to provide for different communications range, power, and/or protocol for communications of data outside the patient's body as compared to communications through the patient's skin and any intervening internal tissue. The communications interface 94 may be wired, whereas the communications interfaces 90 may be wireless. The communications interfaces 90, 94 of the transdermal patch 86 may be similar or identical or may be the same single wireless communications interface. Bluetooth or Bluetooth BLE may be used.

The transdermal patch 86 is an example of a remote device. Similarly, any of the remote devices 100 can be configured to communicate with the biochip 10 via a suitable communications interface onboard the remote device 100.

A remote device 100 receiving data originating from the biochip 10 can store such data in local memory and transmit such data via a wide-area network 102, such as a healthcare facility's intranet and/or the Internet, to a networked storage system 104, which may be termed cloud storage. Data stored at the networked storage system 104 can be made accessible to any remote device 100 operated by an individual or organization concerned for the wellbeing of the patient.

Figure 7:
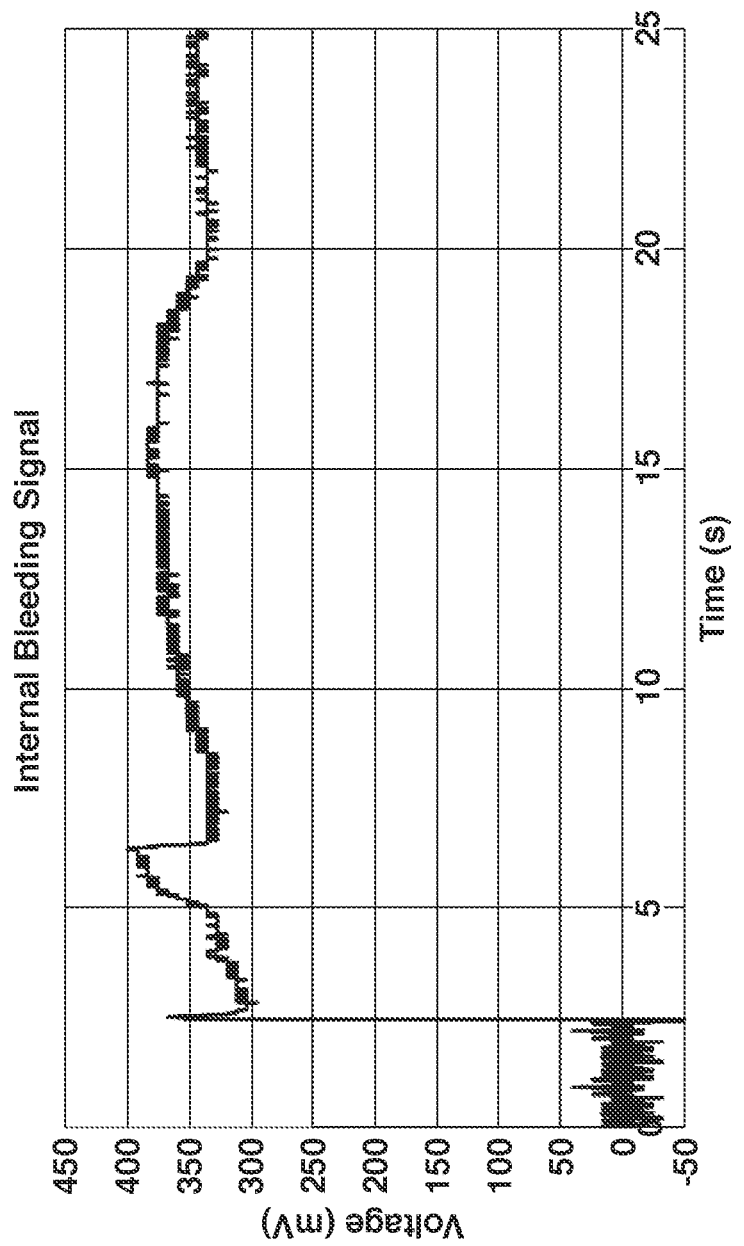
FIG. 7 is a graph a signal measured by the biochip.

Any of the remote devices 100 can be configured to output the data in various ways. In one example, the data is displayed on a chart or graph, such as the plot of voltage vs time shown in FIG. 7. A remote device 100 can be configured to provide access to raw data. Tools for trend analysis may be provided. Further, one of the remote devices 100 and networked storage system 104 can be configured to perform aggregations or comparisons of data from various patients. A trained healthcare professional may then use the data to monitor patient health, predict possible developments of postoperative complications, and undertake interventions if needed.

In other embodiments, wireless communications interfaces can be omitted and data is communicated from the biochip 10 to a remote device 100 or the network 102 through wired communication.

As discussed, data from the biochip 10 can be used to identify the development of postoperative complications. For example, a drop in glucose level may be due to the lack of glucose intake by the individual, bacterial growth, development of ischemia, etc. By monitoring the results obtained from a bacterial sensor of the biochip 10, a trained healthcare professional may be able to narrow down the range of potential complications. For example, the bacterial sensor may detect no development of bacteria. Thus, the professional may review the data associated with a pH sensor to identify a drop in pH to be associated with the development of ischemia and cellular anaerobic respiration. The professional may also look into a protein sensor to identify an increasing trend in protein lactate to diagnose ischemia.

In a further example, data captured by the biochip 10 can be used to identify the development of postoperative complications. For example, a drop in pH may indicate that a bacterial colony has matured in the region, leakage of gastric juice, early signs of ischemic development in the region, inflammation of the area, abnormal healing of the surgical wound, or a combination of such. By monitoring a trend and a rate at which the pH changes, the microcontroller 20 can identify or select probable causes for this change. If the pH has been determined to have gradually increased followed by a gradual decrease, data shows that such a trend is an indication of bacteria colonizing the area and producing basic sub-products, which cause the pH to rise. However, as the bacterial colony grows and matures, the organisms start competing for resources, which causes a drop in the local pH as the bacteria start to release byproducts such as lactic acid. In another example, a sudden pH drop in a specific area can be an indication that gastric juice has leaked from the gastrointestinal system into the peritoneal cavity. In another example, a gradual decrease in the pH can be a sign of ischemic developments in the local area as blood stops flowing to a region and tissues and organs start respiring anaerobically causing materials such as lactic acid to be released in the local area. The microcontroller 20 can be configured to process pH data for such scenarios.

In a further example, data captured by the biochip 10 can be used to identify the development of postoperative complications. For example, it is known that immediately following surgery, the inflammatory markers (e.g., tumor necrosis factor alpha, interleukin-1 beta, interleukin-8, interleukin-12, ADAM 17, C-reactive protein) are at the highest expected levels. The microcontroller 20 can be configured to take a baseline reading immediately following surgery. Trends in inflammatory markers can then be monitored. During normal recovery it is expected that levels of inflammatory markers rapidly drop in the hours following surgery. If the markers are monitored to be increasing or unchanging, it may be an indication that the patient is suffering from a postoperative complication.

Figure 8:
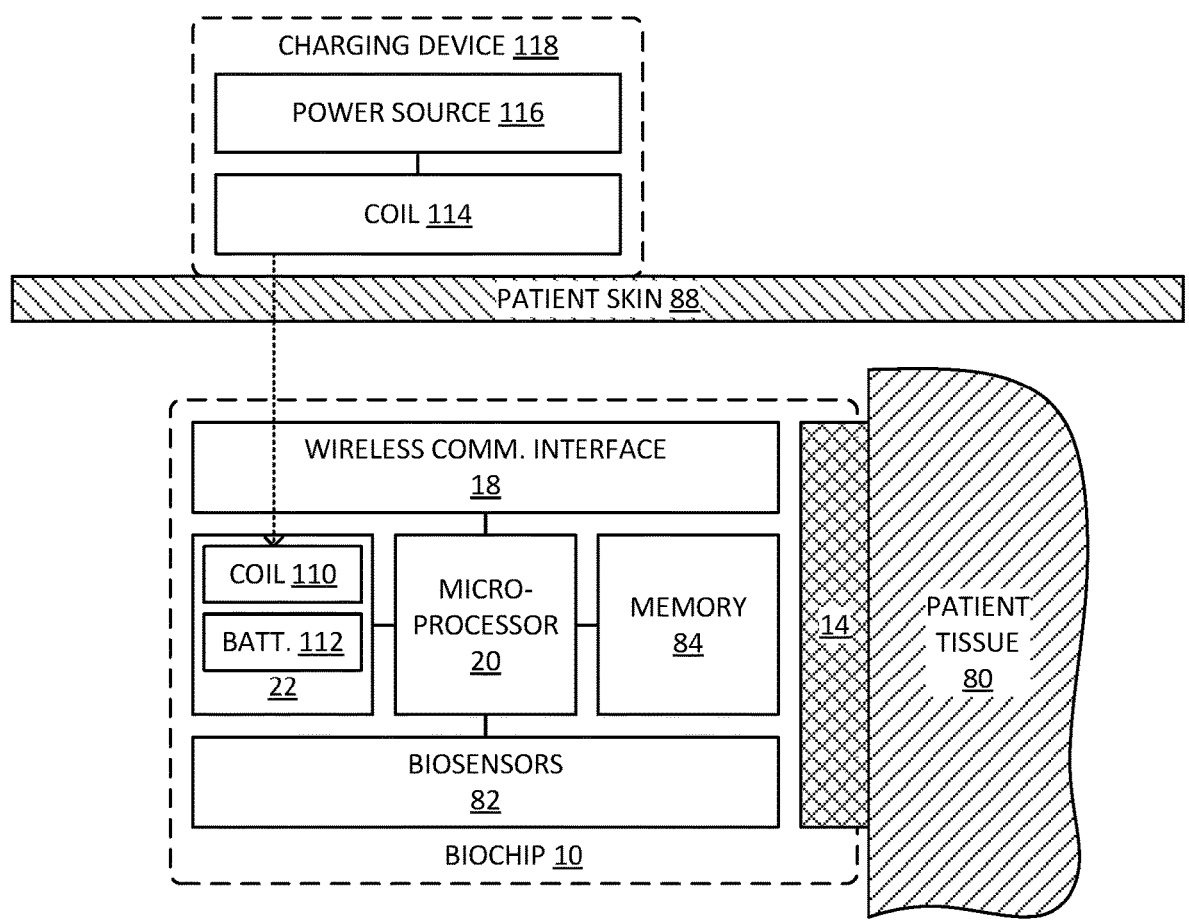
FIG. 8 is a block diagram of a charging device for the biochip.

FIG. 8 shows an embodiment of the biochip 10 undergoing inductive charging. In this embodiment, the power source 22 of the biochip 10 includes an inductive coil 110 connected to a rechargeable battery (or capacitor) 112. Current is induced in the inductive coil 110 by an inductive coil 114 driven by a power source 116 at an external charging device 118 that is placed at a location near the biosensor 10 and outside the patient's body. The power source 116 of the external charging device 118 can include a battery, wall plug, or similar. In other embodiments, the charging device 118 is integrated with a transdermal patch or another kind of remote device.

Figure 9:
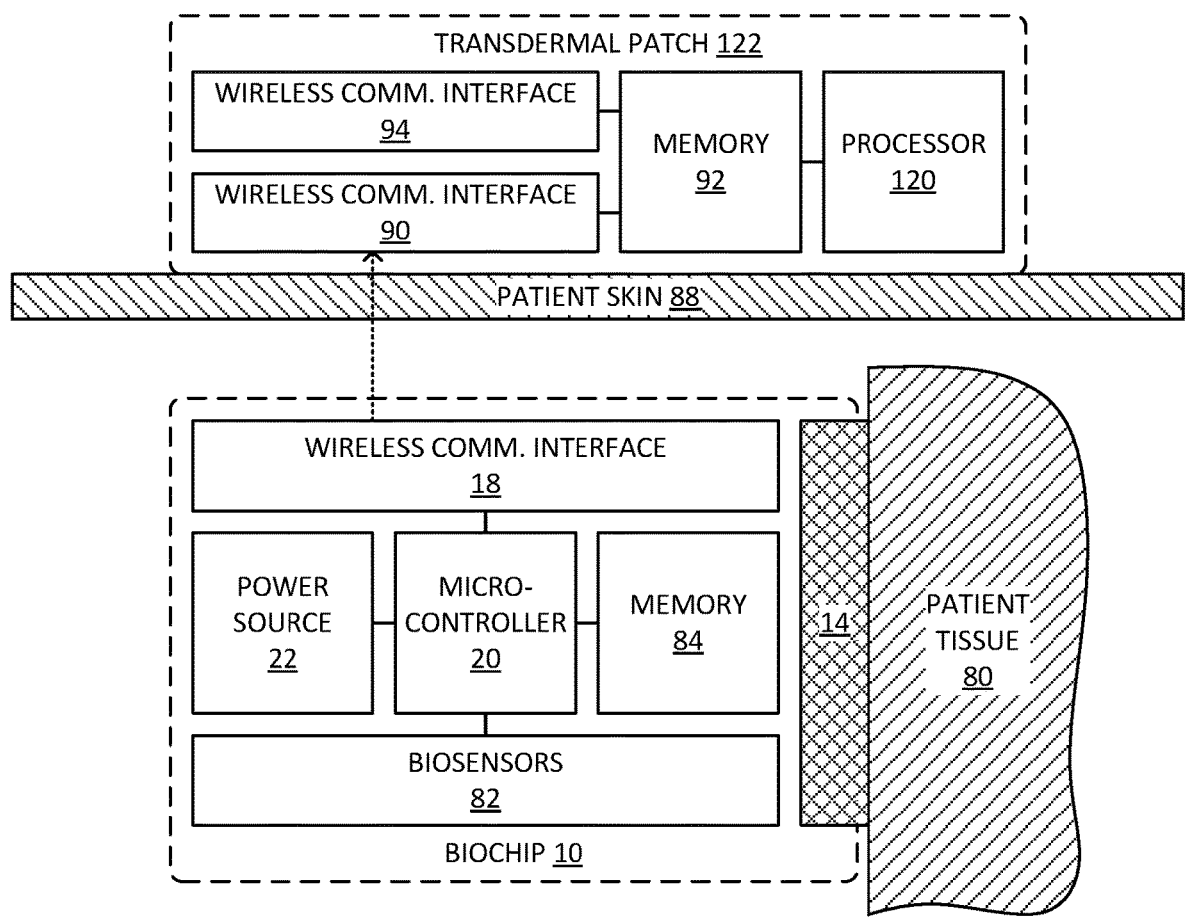
FIG. 9 a block diagram of the biochip and another transdermal patch.

FIG. 9 shows another embodiment of the biochip 10, in which some or all of the analysis of the data is performed in a processor 120 of a transdermal patch 122, which is otherwise similar or identical to the transdermal patch 86 discussed above. In this embodiment, the microcontroller 20 still handles signal detection/measurement to obtain the measured data, and performs a lesser amount of or no analysis on the data. It is contemplated that the processor 120 and microcontroller 20 can split the processing of the analysis on captured data in various ways.

Figure 10:
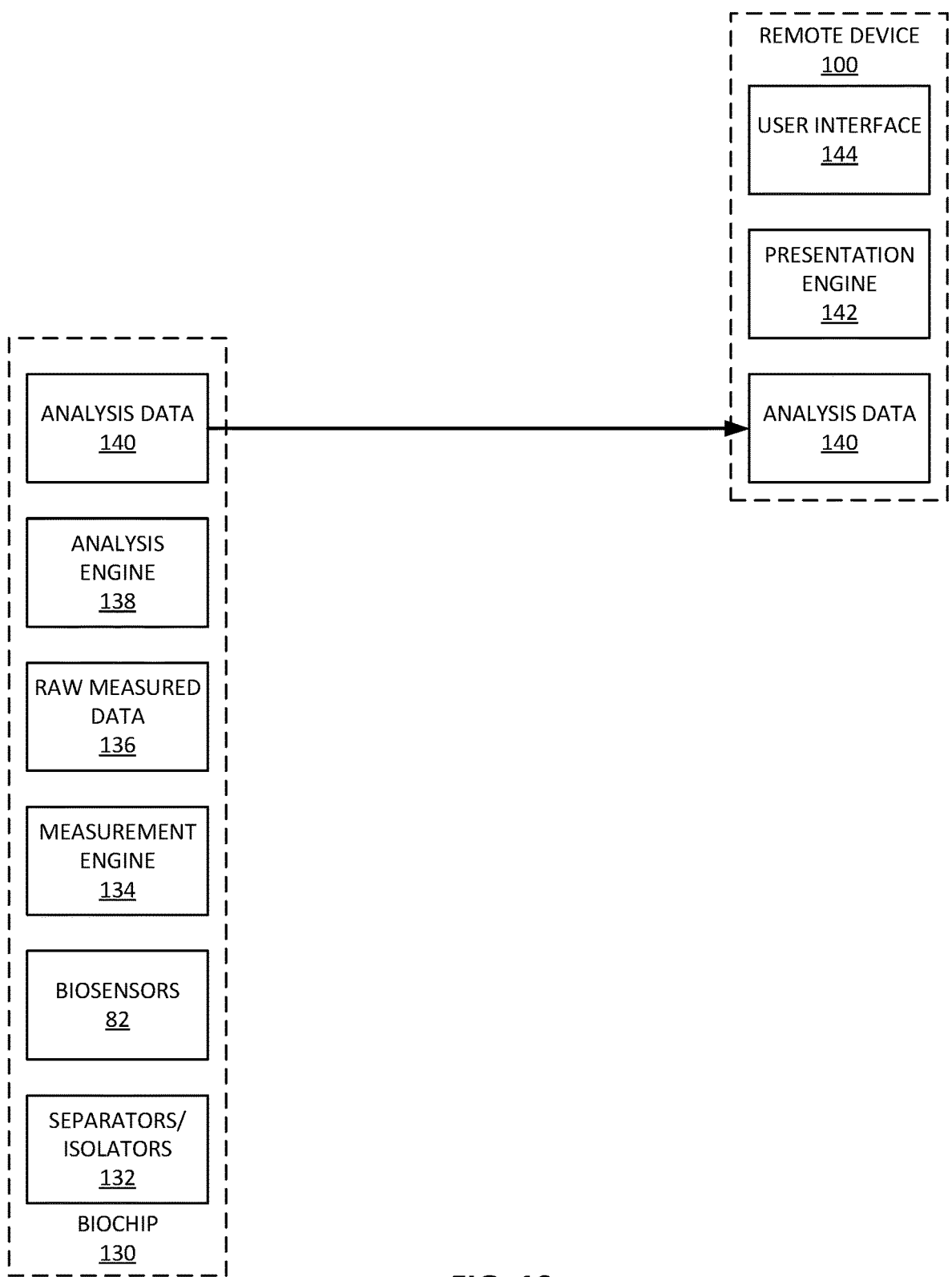
FIG. 10 is a schematic diagram of a sensing, data processing, data storing, communications, and presentation scheme between a biochip and a remote device.
Figure 11:
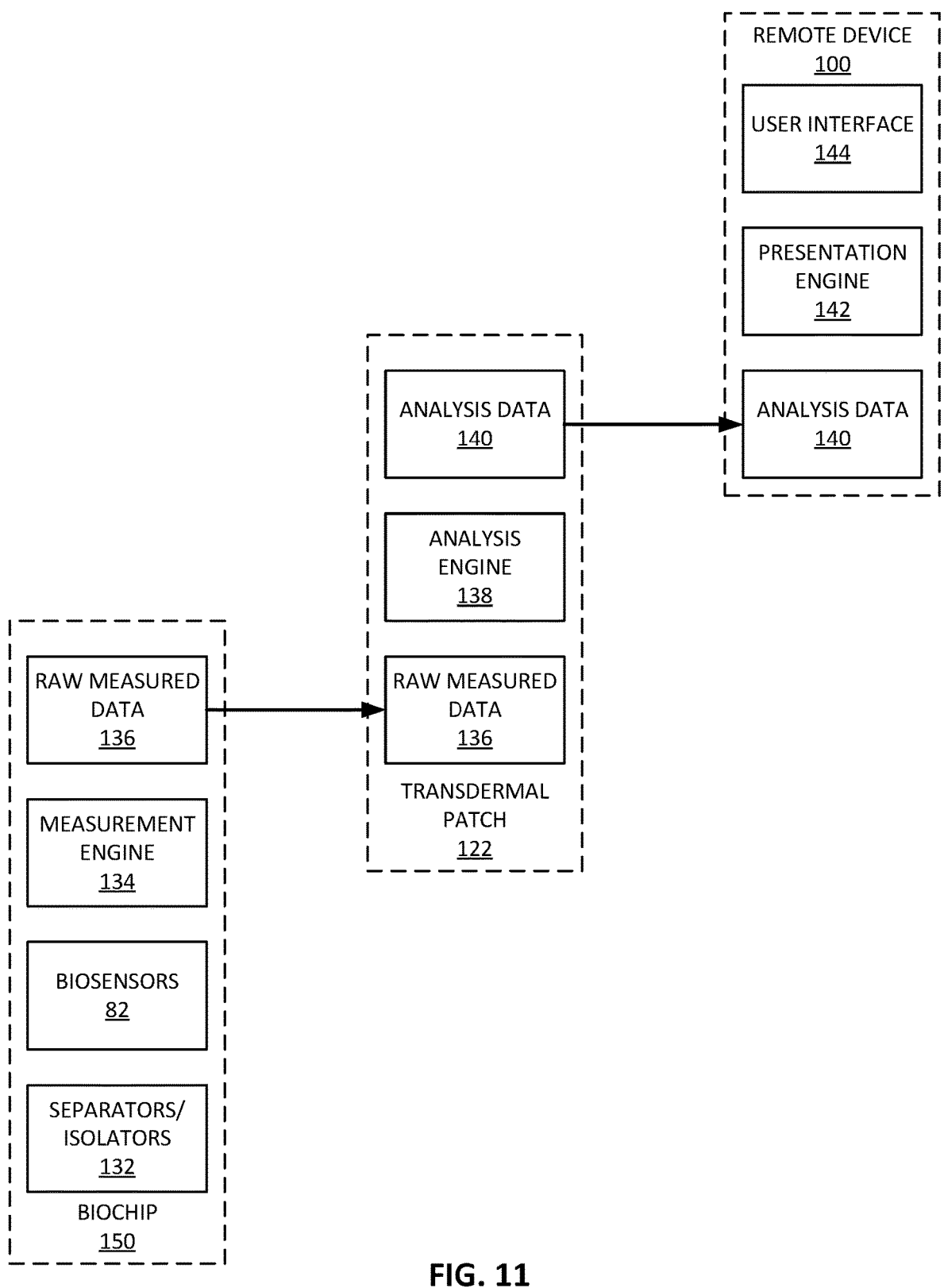
FIG. 11 is a schematic diagram of a sensing, data processing, data storing, communications, and presentation scheme between a biochip, a transdermal patch, and a remote device.
Figure 12:
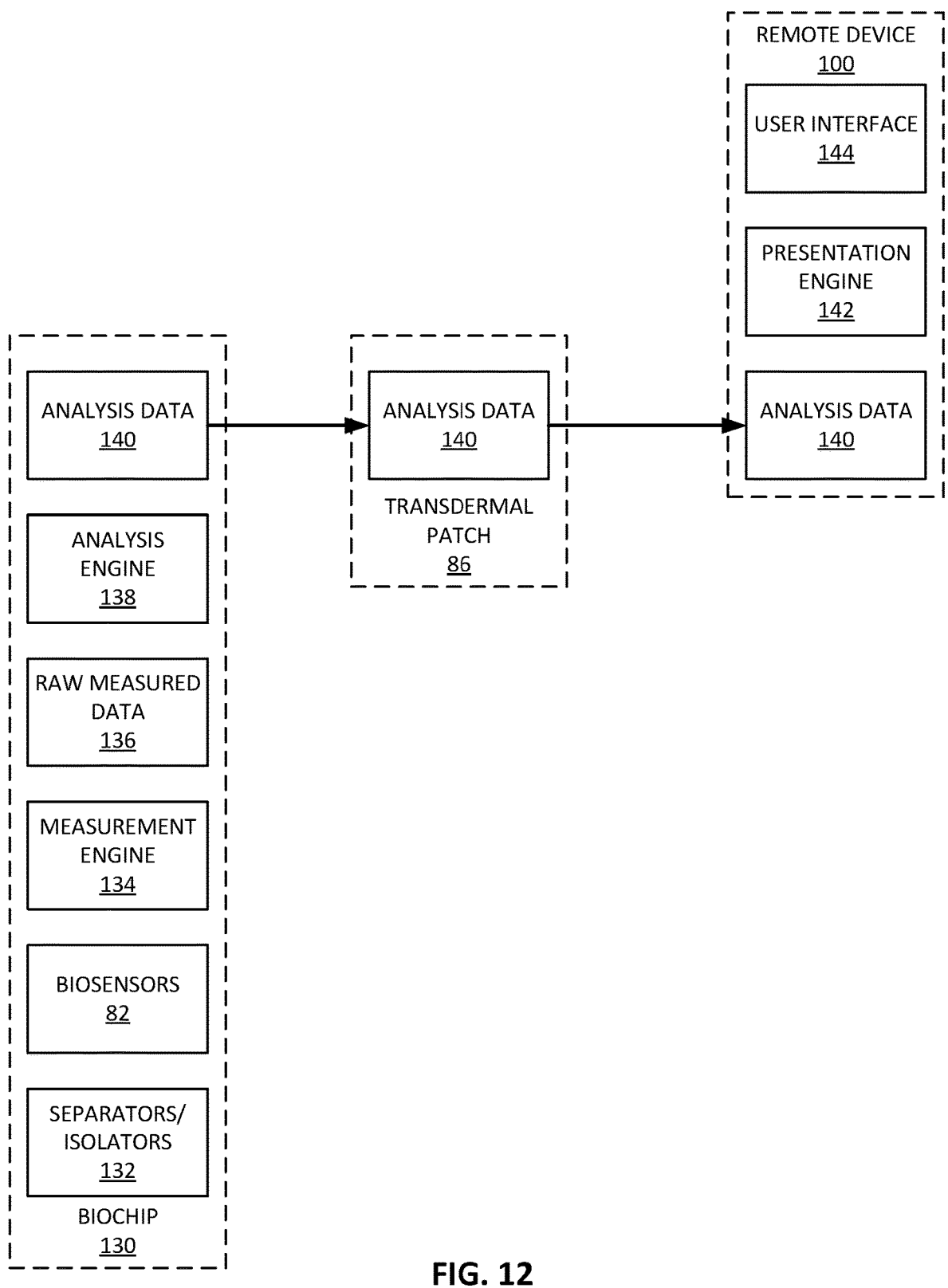
FIG. 12 is a schematic diagram of a sensing, data processing, data storing, communications, and presentation scheme between a biochip, another transdermal patch, and a remote device.

FIGS. 10, 11, and 12 show sensing, data processing, data storing, communications, and presentation schemes according to various embodiments.

FIG. 10 illustrates functional blocks of a biochip 130, which can implement features of any of the biochips discussed herein (e.g., biochip 10). The biochip 130 includes separators or isolators 132 that separate or isolate analytes from bodily fluid and provide such to biosensors 82. Examples of separators or isolators 132 include polymer filter structures and charged channel walls, discussed below. Examples of biosensors 82 include electrodes or other device for measuring an electrical property, as discussed elsewhere herein. The biochip 130 further includes a measurement engine 134, which can be implemented as a program executable by the microcontroller 20. The measurement engine 134 is configured to measure an electrical property, such as voltage, current, resistance, resistivity, conductivity, circuit frequency, time, electrical induction, capacitance, or a combination of such, sensed at the biosensors 82. The measurement engine 134 stored raw measured data in memory at the biochip 130. The biochip 130 further includes an analysis engine, which can be implemented as a program executable by the microcontroller 20, including in the same program as the measurement engine 134. The analysis engine 138 takes measured data and processes it according to an analysis, such as any of those discussed herein. The analysis engine 138 outputs analysis data 140 to memory of the biochip 130. Analysis data 140 is transmitted wirelessly (or via a wired connection) through suitable communications interfaces of the biochip 130 and a remote device 100 for storage at memory in the remote device 100. The remote device 100 includes a presentation engine 142 and a user interface 144 that are executable by a processor of the remote device 100. The presentation engine 142 is configured to generate a presentation, such as a data table, graph, alert, or similar for the analysis data 140. The presentation engine 142 and user interface 144 cooperate to display or otherwise output analysis data 140 in various manners of presentation as discussed elsewhere herein.

FIG. 11 illustrates functional blocks of a biochip 150, which can implement features of any of the biochips discussed herein (e.g., biochip 10). The biochip 150 is similar to the biochip 130 of FIG. 10 and only differences will be discussed in detail. The above description for the biochip 130 and remote device 100 can be referenced. The biochip 150 includes separators or isolators 132, biosensors 82, and a measurement engine 134. However, the biochip 150 lacks the analysis engine 138. Instead, the analysis engine 138 is implemented as an executable program of a transdermal patch 122. The analysis engine 138 receives measured data 136 from the biochip 150, via respective wireless or wired communications interfaces. The analysis engine 138 performs the analysis and outputs analysis data 140 to memory of the transdermal patch 122. The analysis data 140 is then transmitted wirelessly (or via a wired connection) through suitable communications interfaces of the transdermal patch 122 and a remote device 100 for storage and presentation at the remote device 100.

FIG. 12 illustrates functional blocks of the biochip 130, which transmits analysis data 140 through a transdermal patch 86 to a remote device 100. The above description for the biochip 130 and remote device 100 can be referenced. The transdermal patch 86 serves as a wireless and/or wired bridge between the biochip 130 and the remote device 100.

Various applications of the biochip 10 are discussed below.

The microfluidic channels 60 can be configured to detect inflammatory biomarkers, proteins, or enzymes, which may include but are not limited to: ADAM 17, C-reactive protein, tumor necrosis factor alpha (TNF-α), and Interleukin 2, 6, 8, 10. As inflammatory biomarkers move through the microfluidic channels 60, a potential difference is caused in the ion-selective electrodes 62, 64. Such potential difference can be measured by the microcontroller and compared to reference levels to determine whether a dangerous inflammation is developing. Inflammatory markers can be detected by different electrochemical sensors provided to the microfluidic channels 60.

In other embodiments, the biochip 10 can be provided with a three-electrode system consisting of a working electrode, a counter electrode, and a reference electrode. This enables accurate sensing of different biomaterials (e.g., glucose).

Electrodes of biosensors 30, 32, 34 can be configured to detect glucose. This can be done by an enzymatic method involving the use of an enzyme, such as glucose oxidase, a mediator and a catalyst coating that can be placed on the surface of the electrodes or embedded in polymer coating surrounding the electrodes. Glucose detection can also be achieved by a non-enzymatic method including the use of nanoparticles such as copper, gold, or copper oxide as coating. The particles may be immobilized onto the electrodes by a polymer matrix such as polymacon, polyethylene oxide, polyvinylpyrrolidone, polyacrylamide, and/or Nafion™.

Cell metabolism may be monitored by locally detecting the release of biomarkers, such as proteins, for example, lactase. The monitoring can be achieved as well by monitoring the local changes of glucose level versus the body's systematic glucose level to determine the possible development of bacterial culture or the lack of blood supply to the area.

In another application, the biochip 10 may be used for detecting the existence of unwanted foreign objects inside the body. This can be done by correlating a local increase in the local inflammatory markers versus a systematic look into the body's inflammatory markers, such as C-reactive protein.

The biochip 10 is capable of detecting anastomotic leaks within the abdominal region. The biochip 10 may be used to detect fluid leakage in the peritoneal cavity of patients having undergone upper gastrointestinal (UGI) surgery or other bariatric surgery.

In another application of the biochip 10, a potential detection method involves inducing an electrochemical reaction to induce a voltage signal. A potential difference may arise due to the use of different materials for electrode pairs 62, 64, such as gold-platinum or titanium-gold. Different materials have different potentials and work functions and the difference between them allows a voltage to be measured by a voltmeter in the microcontroller 20.

In an example use case, after a patient had an anastomotic surgery, a breakage along the stapling line of the gastrointestinal tract occurs. This could result in the immediate release of gastric fluid into the body. As soon as the gastric fluid comes in contact with the electrodes 62, 64 in the microchannel or electrodes at biosensors 30, 32, 34 on the top layer 50, the microcontroller 20 measures the incoming fluid as a voltage signal indicating that the fluid has been released into the body. The microcontroller 20 controls the wireless communications interface 18 to transmit data indicative of the fluid release to a remote device, outside the body, such as a transdermal patch, located on the skin over in the vicinity of the surgical site. The data can then be provided to other remote devices, such as mobile devices belonging to the surgeon, physician, veterinarian, patient, or other caregiver. Thus, all relevant people are quickly and efficiently alerted to the detection of the gastric fluid.

Figure 13:
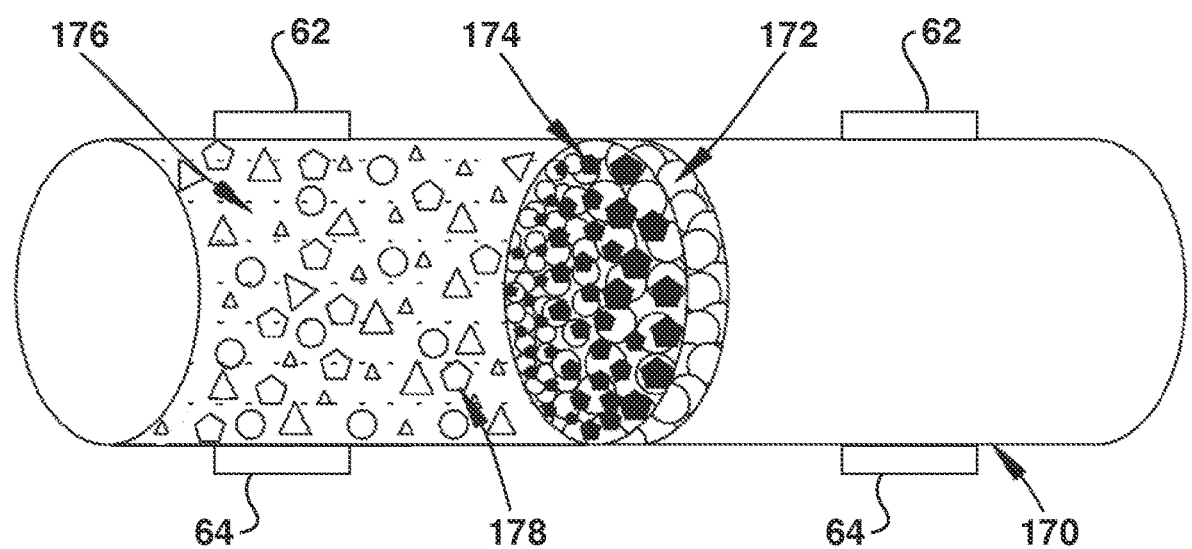
FIG. 13 is a diagram of a microchannel for measuring biomarkers using flow rate.

FIG. 13 shows an embodiment of a microfluidic channel or microchannel 170 configured to detect and/or quantify biomarkers using flow rate. The microfluidic channel 170 can be provided to the biochip 10, as a microfluidic channel 60, can be provided in a different biochip, or can be provided in a different structure. For sake of explanation, the microfluidic channel 170 will be discussed in the context of the biochip 10, though this is not intended to limit the present invention. A biochip using the microfluidic channel 170 has many of the same features, aspects, applications, and advantages of the other biochips discussed herein.

In this embodiment, substrates are placed directly in microfluidic channels or in polymer structures disposed in the microfluidic channels, so as to physically obstruct flow through the microfluidic channels. Polymer structures can include materials such as polyacrylamide, poly lactic-co-glycolic acid (PLGA), polycaprolactone, polyorthoester, polyethylene glycol, and similar. If an analyte (e.g., enzyme, catalyst, antibody, etc.) matching a substrate is present in a bodily fluid analyte within a microchannel, the matching analyte will consume or interact with the substrate within the microchannel to reduce or eliminate physical restriction to flow. Consequently, flow though the microchannel will occur or will increase. If a matching analyte is not present in the bodily fluid analyte, the respective substrate will not be consumed, and consequently will not contribute to reducing or eliminating physical restriction to flow. Flow will not occur or will not increase. Therefore, isolation and detection of analytes can be achieved by examining the presence and/or degree of flow of the analyte through a microfluidic channel. In addition, the rate at which a substrate is consumed is directly proportional to the concentration of the respective analyte in the bodily fluid. Hence, the concentration of an analyte can be calculated by measuring flow rate. The analysis performed by the microcontroller 20 or at a remote device (e.g., the transdermal patch) is configured to relate flow rate through the microfluidic channel 170 to analyte concentration.

Figure 14:
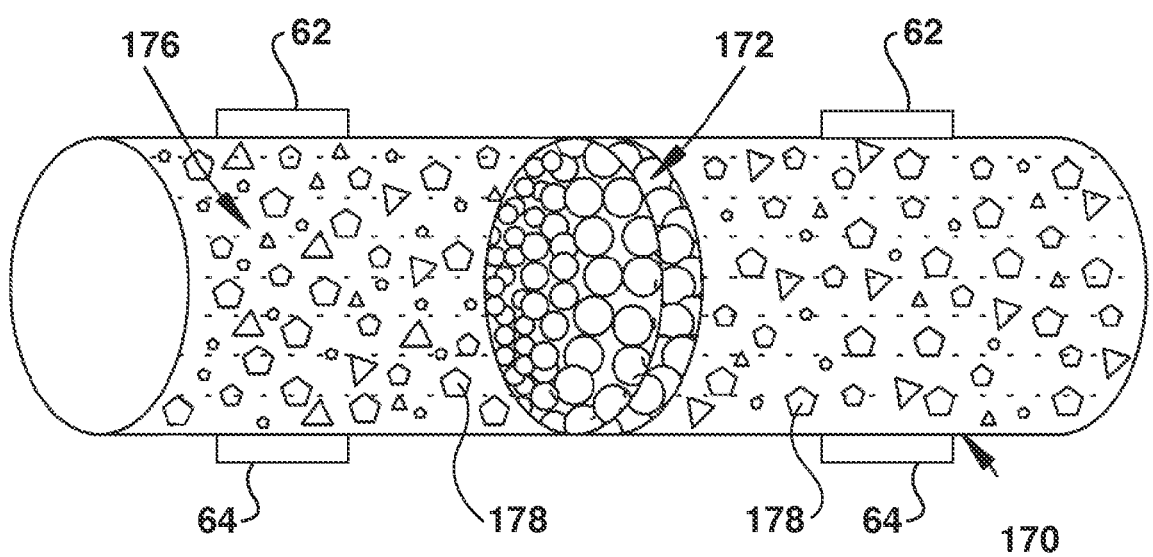
FIG. 14 is a diagram showing flow in the microchannel of FIG. 13.

With reference to FIG. 13, the microfluidic channel 170 includes a polymer or gel matrix 172 (or other polymer structure) that contains one or more substrates 174. The gel matrix 172 with substrates 174 is located at a position in the microchannel 170 that obstructs or reduces flow through the microchannel 170. The gel matrix 172 can be adhered to the inside wall of the microchannel 170. The gel matrix 172 with substrates 174 can form a plug or flow restrictor. Bodily fluids (e.g., peritoneal fluid) containing one or more analytes 176, such as one or more enzymes, is introduced into the microfluidic channel 170. Matching analytes 178 consume the substrates 174, thereby creating passages in the gel matrix 172 or dislodging the gel matrix 172 from the wall of the microchannel 170. Consequently, fluid flows past the gel matrix 172, as shown in FIG. 14.

Figure 23:
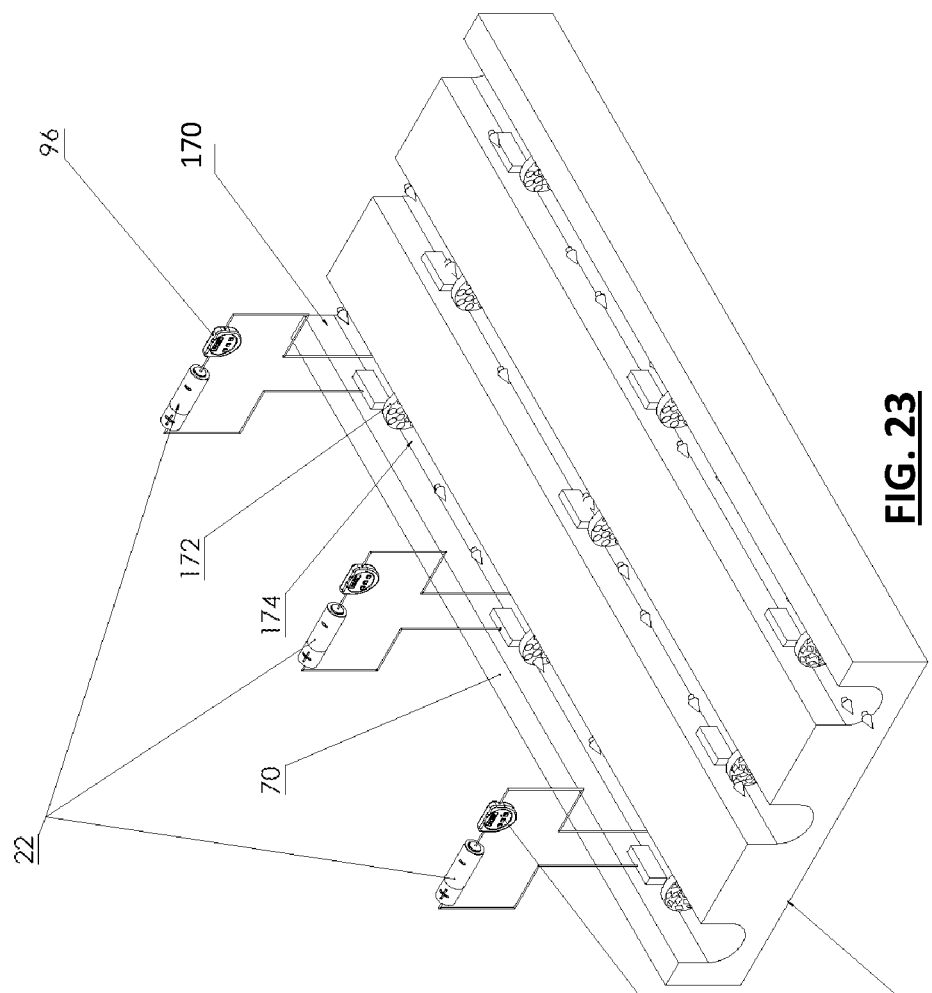
FIG. 23 is a perspective view of microfluidic channels for measuring flow rate.
Figure 24:
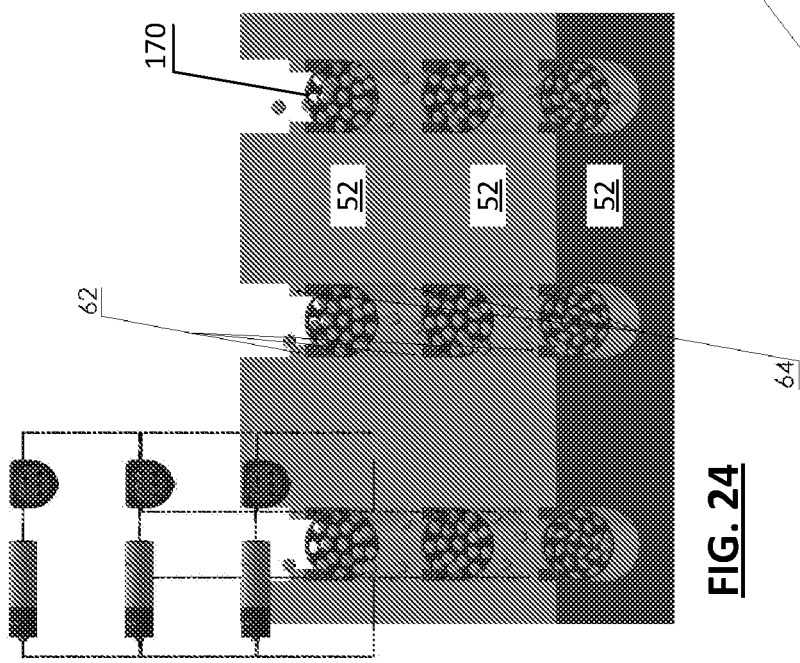
FIG. 24 is an end view of FIG. 23.

With reference to FIGS. 23 and 24, the flow rate of the fluid along the microfluidic channel 170 can be measured using electrode pairs 62, 64 (FIG. 5) across the channel. As the fluid flows enters the channel through the membrane 66, it first comes into contact with two pairs of electrodes 62, 64 placed on the opposite sides of the microchannel 170 these electrodes associated with a timer in the microcontroller 20. As the electrodes are exposed to an ionic fluid, a signal is obtained and the timer is initiated and read (time T1), as shown by timer 96. The fluid flow will then come in contact with the substrate 174 that has been placed inside the polymer matrix 172 to block the flow of the ionic fluid. If the ionic fluid bears the analyte that can interact or consume the substrate 174, the fluid will eventually flow through the porous polymer 172 (FIG. 14) and a subsequent pair of electrodes 62, 64. The subsequent pair of electrodes 62, 64 are placed on the opposite sides of the microchannel 170 and are associated with the timer in the microcontroller 20. As the electrodes are exposed to the ionic fluid, a signal is obtained and the timer is read (time T2), as shown by timer 98. The microcontroller 20 then computes a time difference between the first time measurement and the second time measurement (i.e., T2-T1). The time it takes for the flow to go through the porous polymer 172 is dependent on the concentration of the analyte. The data can therefore be analyzed to correlate the time it took between the two pairs of electrodes to the concentration of the analyte being targeted. This process can be repeated any number of times along a microfluidic channel 170. In addition, control methods can be placed in the microchannel 170 to prevent false readings that can be caused by an unwanted biomarker interacting with a substrate 174. These include filling the microchannels with synthesized materials that can interact, denature, kill, or prevent the unwanted biomarker from interacting with the substrate 174. As shown in FIG. 24, stacks of channel layers 52 defining microchannels 170 there-between can be used to measure various analytes at the same time and in the same environment.

Figure 15:
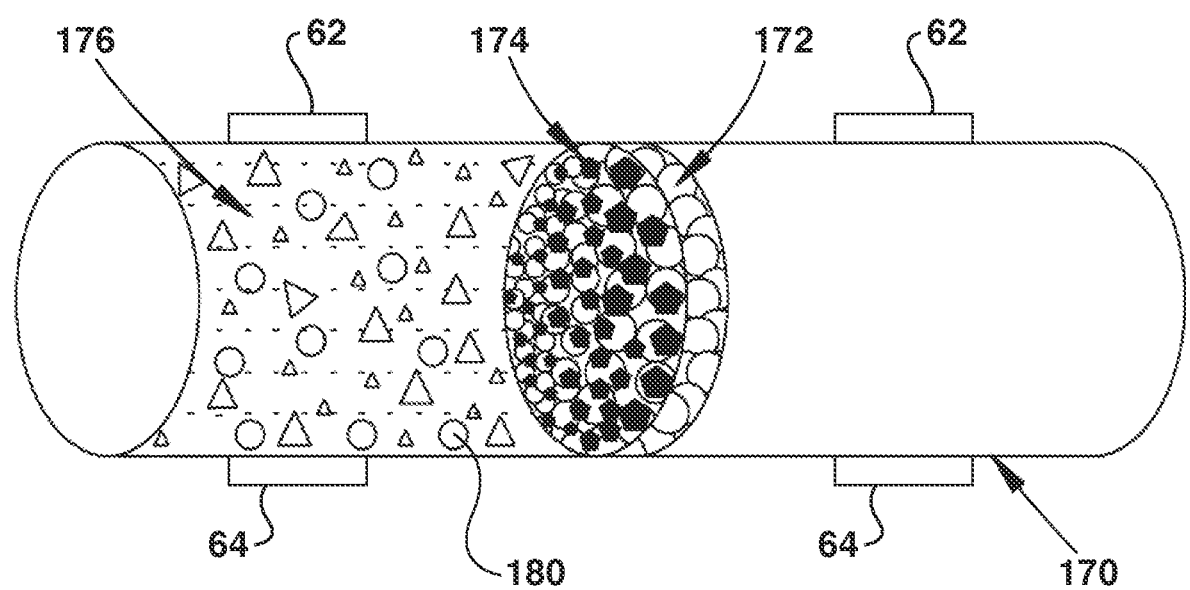
FIG. 15 is a diagram showing no flow in the microchannel of FIG. 13.

As shown in FIG. 15, various analytes 180 present in the fluid do not match the substrates 174 in the gel matrix 172. Accordingly, fluid does not flow past the gel matrix 172.

Figure 16:
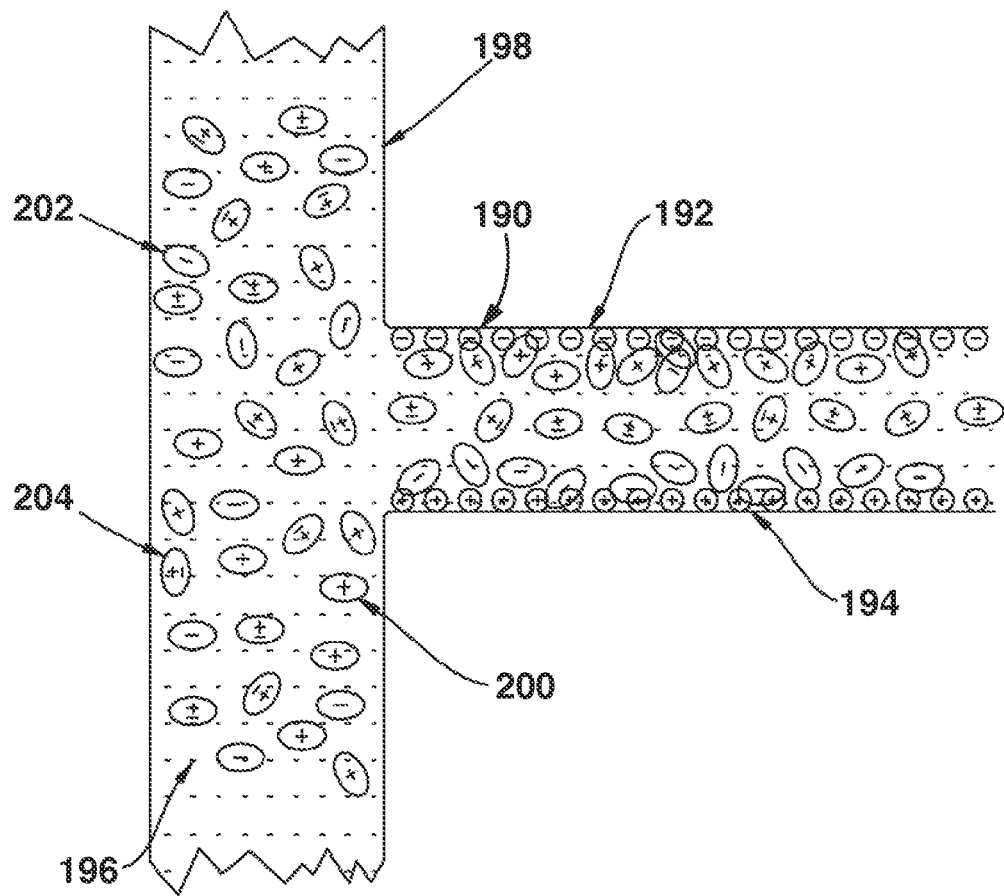
FIG. 16 is a diagram of a microchannel for separation/isolation of biomarkers using charge.

FIG. 16 shows an embodiment of a microfluidic channel or microchannel 190 configured to detect, quantify, separate and filter biomarkers using charge. This can be useful as a sample preparation technique to, for example, prevent biofouling or unwanted chemicals from affecting measurements. The microfluidic channel 190 can be provided to the biochip 10, as a microfluidic channel 60, can be provided in a different biochip, or can be provided in a different structure. For sake of explanation, the microfluidic channel 190 will be discussed in the context of the biochip 10, though this is not intended to limit the present invention. A biochip using the microfluidic channel 190 has many of the same features, aspects, applications, and advantages of the other biochips discussed herein.

The microfluidic channel 190 has a negatively charged wall 192 and a positively charged wall 194 positioned opposite the negatively charged wall 192. A biological fluid 196, is introduced to the microfluidic channel 190 from, for example, a communicating microfluidic channel 198, which in this example forms a T-junction with the microfluidic channel 190. The fluid 196 contains one or more analytes containing positively, negatively, or neutrally charged substances (e.g., proteins), one or more of which is a biomarker of interest. As fluid 196 flows through the microfluidic channel 190, positively charged analytes 200 migrate to the negatively charged wall 192 and negatively charged analytes 202 migrate to the positively charged wall 194. Neutrally charged analytes 204 are not influenced by charge and may tend towards the middle of the microfluidic channel 190.

Figure 17:
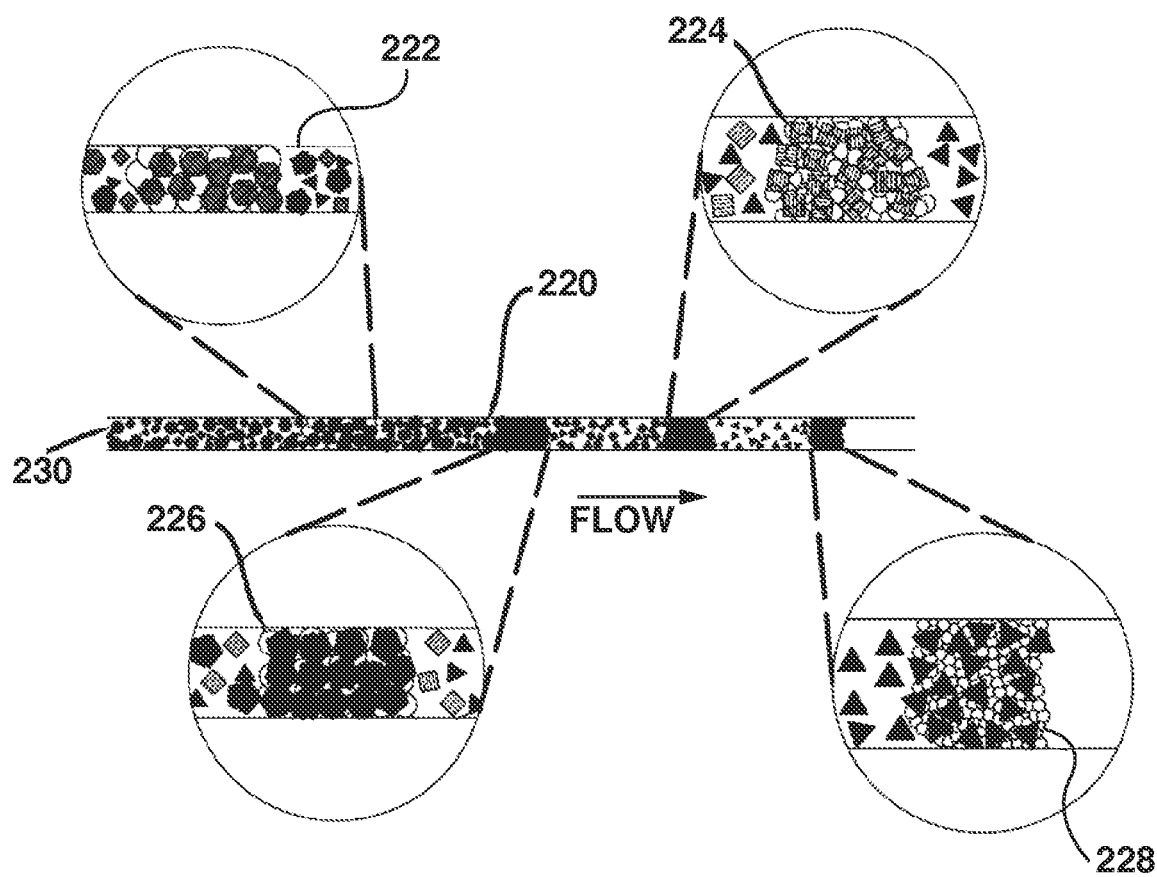
FIG. 17 is a diagram of a microchannel for separation/isolation of biomarkers using size discrimination.

FIG. 17 shows an embodiment of a microfluidic channel or microchannel 220 configured to separate and/or isolate biomarkers using size to discriminate. This can be useful as a sample preparation technique to, for example, prevent biofouling or unwanted chemicals from affecting measurements. The microfluidic channel 220 can be provided to the biochip 10, as a microfluidic channel 60, can be provided in a different biochip, or can be provided in a different structure. For the sake of explanation, the microfluidic channel 220 will be discussed in the context of the biochip 10, though this is not intended to limit the present invention. A biochip using the microfluidic channel 220 has many of the same features, aspects, applications, and advantages of the other biochips discussed herein.

In this embodiment, one or more polymer structures are disposed in the microfluidic channel 220. Each polymer structure is a porous structure that defines pores of a specific and unique size or size range. Examples of polymers include, but are not limited to, polyacrylamide, poly lactic-co-glycolic acid, or polyorthoester. The polymer structures disposed in the microfluidic channel 220 may be positioned as shown by polymer structures 70 shown in FIG. 5.

The microfluidic channel 220 contains various polymer structures 222, 224, 226, 228 along at least a portion of its length. Four polymer structures are used for example only, and any number of polymer structures can be implemented. Each polymer structure 222, 224, 226, 228 defines a different pore size or size range selected to allow flow of fluid, but trap one or more analytes of interest. The polymer structures 222, 224, 226, 228 are arranged from largest to smallest port size/range in the direction of fluid flow. Hence, while a larger analyte is trapped by a larger pore size, a downstream polymer structure has a pore size that captures smaller analytes.

When bodily fluid 230, flows into the microfluidic channel 220, one or more analytes in the fluid are filtered by the pores in the polymer structures 222, 224, 226, 228. The polymer structures 222, 224, 226, 228 filter the analytes progressively in deceasing size in the direction of fluid flow. Ultimately the fluid in the microfluidic channel 220 is separated into regions containing substances of particular sizes and/or size ranges, where such regions are bounded by the polymer structures 222, 224, 226, 228. Size separation of analytes results. A separated analyte can be subsequently routed to another microchannel or brought into range of a sensor (e.g., electrodes) for measurement.

Figure 18:
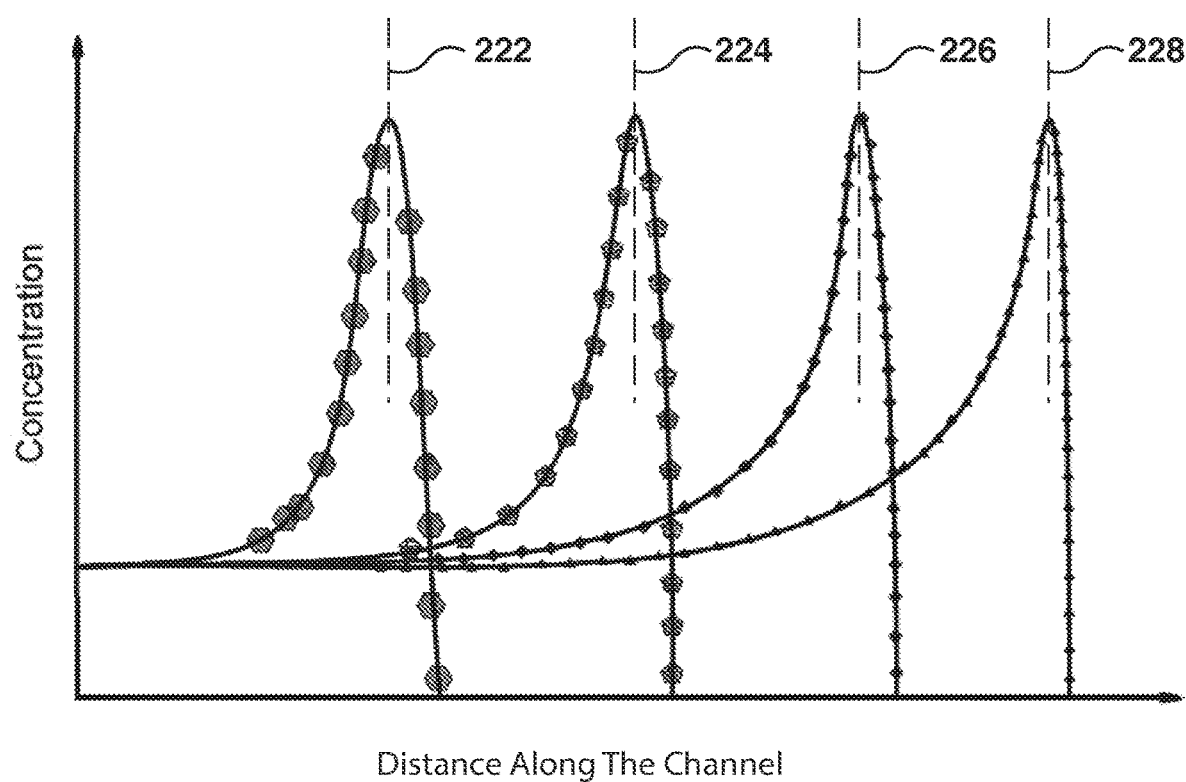
FIG. 18 is a graph of concentrations of different biomarkers in the microchannel of FIG. 17.

FIG. 18 shows concentrations of different biomarkers isolated by the microfluidic channel 220. As can be seen, the concentration of each biomarker reaches a maximum at the location of the respective polymer structures 222, 224, 226, 228.

Figure 19:
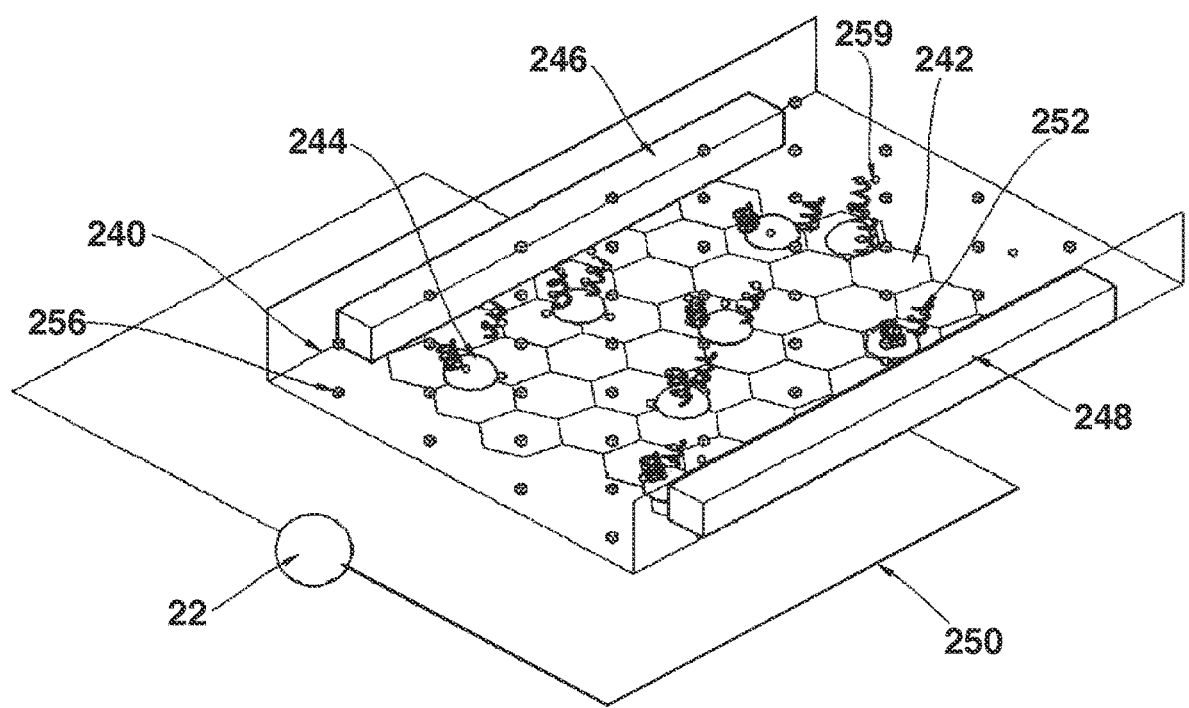
FIG. 19 is a diagram of a microchannel for measuring biomarkers using aptamers, antibodies, or combination of such.

FIG. 19 shows an embodiment of a microfluidic channel or microchannel 240 configured to detect and/or quantify biomarkers using aptamers, antibodies, or a combination of such. The microfluidic channel 240 can be provided to the biochip 10, as a microfluidic channel 60, can be provided in a different biochip, or can be provided in a different structure. For sake of explanation, the microfluidic channel 240 will be discussed in the context of the biochip 10, though this is not intended to limit the present invention. A biochip using the microfluidic channel 240 has many of the same features, aspects, applications, and advantages of the other biochips discussed herein.

A nanoparticle sheet 242 including conductive material is disposed at the bottom of the microfluidic channel 240. The nanoparticle sheet 242 can include graphene, carbon nanotubes, silver nanowires, gold nanowires, silicon (intrinsic or doped), polymer, hydrogel, microgel, or similar material, designated at 244. An example material is polypyrrole gel. One or more aptamers, antibodies, or a combination of such 252 are embedded in, disposed on the surface of, or otherwise attached to the nanoparticle sheet 242. The nanoparticle sheet 242 is connected to the power source 22 (e.g., a current source) via a pair of electrodes 246, 248 and intermediate traces, wires, and/or interconnects 250. The pair of electrodes 246, 248 spans the microfluidic channel 240. The aptamers, antibodies, or combination of such 252 are selective against one or more analytes 254. Binding of the analyte 254 to the aptamer, antibody, or a combination of such 252 changes an electrical property (e.g., current, resistance, voltage, etc.) in the nanoparticle sheet 242 and the change in electrical property can be detected or measured at the pair of electrodes 246, 248 by, for example, the microcontroller 20 (FIG. 1). Non-matching analytes 256 do not bind to the aptamer, antibody, or a combination of such 252, and thus do not affect the measured current.

The microcontroller 20 can be configured to map measured current to concentration of an analyte.

In other embodiments, aptamers, antibodies, or combination of such 252 are embedded into a wall of the microfluidic channel 240 containing or made of conductive material, and the nanoparticle sheet 242 can be omitted.

Figure 20:
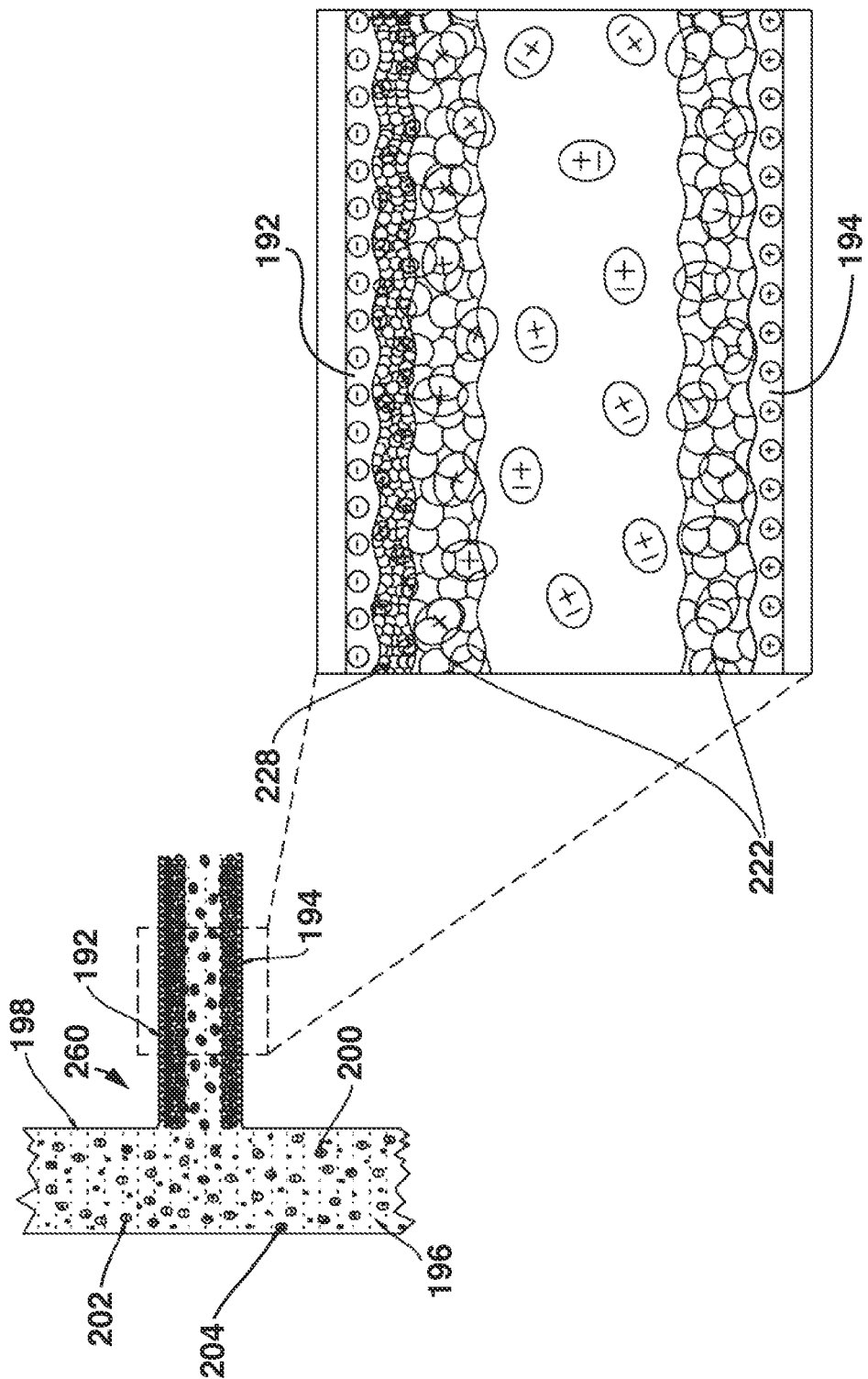
FIG. 20 is a diagram of a microchannel for measuring biomarkers using charge and size discrimination.

FIG. 20 shows an embodiment of a microfluidic channel or microchannel 260 configured to detect and/or quantify biomarkers using charge and size to discriminate. The microfluidic channel 260 combines features of the microfluidic channels 190 and 220, shown in FIGS. 18 and 19, and the description of these embodiments can be referenced for further detail.

The microfluidic channel 260 includes negatively and positively charged walls 192, 194. Disposed on one or both walls 192, 194 are one or more polymer structures 222, 228 having different pore sizes or size ranges. The charged walls 192, 194 separate analytes based on charge, and the polymer structures 222, 228 further separate such analytes based on size.

Figure 21:
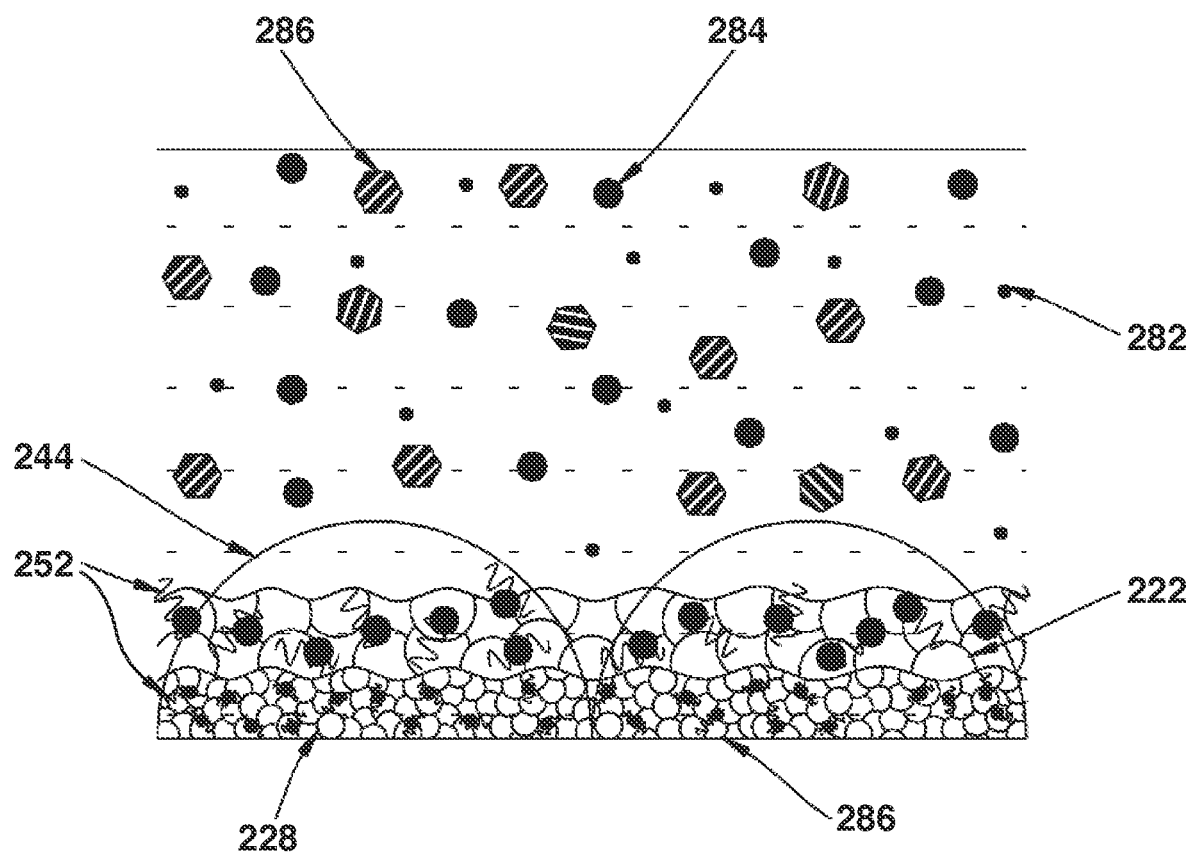
FIG. 21 is a diagram of a microchannel for measuring biomarkers using size discrimination and aptamers, antibodies, or combination of such.

FIG. 21 shows an embodiment of a microfluidic channel or microchannel 280 configured to detect and/or quantify biomarkers using discrimination by size and using aptamers, antibodies, or a combination of such. The microfluidic channel 280 combines features of the microfluidic channels 220 and 240, shown in FIGS. 19 and 21, and the description of these embodiments can be referenced for further detail.

The microfluidic channel 280 includes one or more polymer structures 222, 228 having different pore sizes or size ranges disposed adjacent to one or more aptamers, antibodies, or a combination of such 252 disposed in the microfluidic channel 280. The aptamer, antibody, or combination of such 252 are selective against one or more matching analytes 282, 284, which also meet the one or more size constraints imposed by the polymer structures 222, 228. Analytes 286 that do not match the aptamer, antibody, or combination of such 252 or that do not fit the size constraint are not detected or measured. In the example illustrated, small analytes 282 diffuse through the microgel 244 move through the large-pore polymer structure 222 and into the small-pore polymer structure 228, while larger analytes 282 move only into the large-pore polymer structure 222.

Other combinations of various features of the microfluidic channels 170, 190, 220, 240 are contemplated and within the scope of the present invention.

With reference to FIG. 22, a biochip can be adhered to a medical device, such as a fetal scalp electrode. The biochip can implement any of the techniques discussed herein to augment the functionality of the medical device. In the example of a fetal scalp electrode, the biochip can assist in monitoring analytes/biomarkers in fluids in the uterus and at or near the surface of the scalp. The biochip may wirelessly communicate with a remote device 100 or may communicate via existing wiring used for the fetal scalp electrode.

Various techniques can be used to modify the embodiments discussed above without departing from the present invention. A conductive polymer or hydrogel such as polypyrrole, polyaniline, and polythiophene, provides a broad-spectrum of assay capabilities. Nonconductive hydrogels can be made conductive by embedding or planting several conductive components, such as carbon, metal nanomaterials, conducting polymers, and others, into aqueous gels. If cross-linked and hydrated, polymers such as polyaniline can form an electron-conducting redox hydrogel. As a result, in such a polymer the electrons are transferred between hydrated segments of the polymer that are reducible and oxidizable. In some embodiments, a biosensor can be configured to detect enzyme-labelled immunio-complexes, which can be formed at the surface of a poly-pyrrole coated, screen-printed electrode. The electrode can be made out of gold, silver, or silver chloride, or any safe biodegradable conductive material. An analyte can be captured from the sample to be measured, and complexed with an enzyme labeled antibody and then measured in a controlled environment. In some embodiments, the aforementioned biosensor can obtain its responses from the change in redox conditions. The biosensor detects a change in potential because of the activation of receptor-target complexes, which are formed at the surface of a conductive polymer layer, such as polypyrrole or other material, which is attached to an electrode. Such a biosensor can include conductive polymer, which is coated with specific bio-receptors, with a metal electrode such as gold, silver, or others on a polymer substrate, such as polyethylene terephthalate, PDMS, or others coated with the conductive polymer and specific bio-reagents. Using such a technique, the separation of blood cells and plasma may not be necessary. Therefore, the analytes in the blood or specific bodily fluid being detected can bind with the antibody/antigen directly. Using this technique, separating blood cells from plasma is may not be necessary, as the biosensor is specific to proteins on cell surfaces and plasma protein components, depending on the implementation of the biosensor. As every protein has its respective antibody, this enables the biosensor to carry out specific detection of the target proteins. This technique can identify and quantitate various proteins of interest.

The detection technique used to identify various proteins can also use three electrodes: a sensing electrode, a counter electrode, and a reference electrode. These electrodes can be iridium oxide, iridium, silver, and/or silver chloride. These electrodes can be patterned on a glass substrate or a polymer substrate such as PDMS. With the placement of specific antibodies in the substrate, the antibody-protein complex causes a potential difference between the sensing and the counter electrode, which indicates the presence of such a protein/biomarker in the system. The antibodies are mechanically entrapped into the lattice of a highly cross-linked synthetic polymer by polymerizing the synthetic monomers in an aqueous solution in the presence of the antibody that is to be embedded in the polymer. This in turn indicates the kind of complication occurring as the potential difference will only occur when the specific antibody-protein complex forms (i.e., only one protein passing through the system will result in a potential difference of a specific range that can indicate that the protein is in the system). The counter and sensing electrodes develop a potential depending on the activity or concentration of a specific protein, biomarker, or analyte in the solution.

Other techniques of detection do not use enzymatic targets, such as bio-barcode assays. This technique is a type of assay based on magnetic particles with monoclonal antibodies, which would specifically bind to a target and nanoparticles modified with oligonucleotide strands. The barcode strands released from the nanoparticle surfaces can be used as a method of amplification in order to detect the target needed quantitatively. Gold nanoparticles can be used in order to provide a significant amplification of the electrochemical signal. The nanoparticle can be large in its surface area in order to bind a large number of aptamers, which would lead to substantial amplification and a high level of detection for the analyte in question. The aptamers' specific three-dimensional structures allow them to bind to their targets. Using this technique, an aptamer can be labeled with a redox species, which can be used as signal transducers. Aptamers have the added advantage of being resistant to denaturation and degradation, and their binding affinities and specificities can be easily manipulated and significantly improved by various embodiments of the present invention discussed herein. They can also be modified with various functional groups and/or tags that allow covalent, direct immobilization on biochips, which can result in highly ordered receptor layers.

Other techniques include microgravimetric techniques on piezoelectric quartz crystals, which depend on the change of the oscillation frequency of the crystal when the mass changes at its surface due to receptor-target binding. Such a technique uses a quartz crystal microbalance and the change of the oscillation frequency is the signal that is detected. Specific weight labels such as aptamers with functionalized gold nanoparticles can be used in order to amplify the binding reaction on the quartz crystal microbalance surface. Quartz crystal microbalance offers a high sensitivity, real-time data, and cost-effective method for detection.

Other techniques include a plasmon-polariton fiber-tip-probe, with a single gold nanorod attached to the end of the tip. The gold nanorod can be functionalized with antibodies complementary to the analyte protein to be detected. When proteins attach to the antibody, oscillations of the conductive electrons in the gold nanorod create a resonant scattering signal. Due to the size of the nanorod, it can also be used inside cells without substantially disturbing cell systems. This technique is label-free, not requiring protein labeling such as the use of fluorescence.

Other techniques include the use of short unstructured peptides as aptamers instead of antibodies. These peptides are stable and resistant to harsh environments, can be easily and cheaply be synthesized, and are easier to engineer than antibodies at the molecular level making them suitable for biosensor use. The peptides can be attached to gold plates and protein detection can be identified and quantified using techniques, such as quartz crystal microbalance, cyclic voltammetry and electrical impedance spectroscopy.

The present invention may have applications beyond those described above. Various embodiments may be useful in blood sugar monitoring of diabetic patients, wherein the detection of (severe) hypoglycemia or hyperglycemia is immediate or relatively immediate. Various embodiments may be applied to the early detection of urea and creatinine in the peritoneal cavity, which may be indicative of urinary tract injuries during a postoperative period after laparotomy or laparoscopy. Various embodiments may be used in the detection of onsite or systemic tumor markers for early diagnosis of some tumors or to rule out the recurrence of malignancies with known markers. Various embodiments may be capable of increasing the effect of radiotherapy through application of radiotherapy sensors that may increase the intake level of radiation at an affected tumor site. Various embodiments may have applications in the assessment of fetal wellbeing through monitoring of fetal pH high-risk pregnancies.

The embodiments discussed above may include additional or alternative techniques for fluid detection, such as potentiometric sensors (e.g., ion-selective field effect transistors), amperometric sensors, piezoelectric sensors, electrocardiogram (EKG), and/or electromyography (EMG) sensors.

Various biosensors discussed herein can be used in other applications beyond the biochips discussed, including in vivo, ex vivo and in vitro applications.

The biochip of the present invention may have advantages of biocompatibility, biodegradability, low-current detection, high sensitivity, remote power, secure wireless communications, real-time monitoring, low cost, small size, and versatility to operate on various/multiple fluids. Additionally, the biosensors described herein may advantageously have high sensitivity and fast/quick detection of biomarkers with very low current needed for detection operations. This may be useful for low-power implanted applications, where the biochip's power can be better used for wireless data transfer.

Further advantages include the ability to monitor for postoperative complications in animals, children, and other individuals who cannot communicate pain or alarming postoperative symptoms well. Earlier interventions and improved outcomes may be possible.

While the foregoing provides certain non-limiting example embodiments, it should be understood that combinations, subsets, and variations of the foregoing are contemplated. The monopoly sought is defined by the claims.

What is claimed is:

1. A device for detecting postoperative complications in a patient, the device comprising:
    a substrate made of biocompatible or biodegradable material;
    at least one biosensor disposed at the substrate, the at least one biosensor configured to detect or measure at least one analyte in a body of the patient;
    a rigid microfluidic channel defined by the substrate, the rigid microfluidic channel comprising a passage for a fluid, the rigid microfluidic channel containing the at least one biosensor therein, the fluid comprising the at least one analyte;
    a wireless communications interface disposed on the substrate;
    a microcontroller disposed on the substrate, the microcontroller connected to the at least one biosensor and the wireless communications interface, the microcontroller configured to measure at least one signal from the at least one biosensor, perform an analysis on the at least one measured signal, and transmit data from the analysis through the wireless communications interface to a remote device; and
    a power source for powering the wireless communications interface and the microcontroller.

2. The device of claim 1, wherein the at least one biosensor comprises a pair of ion-selective electrodes.

3. The device of claim 1, wherein the rigid microfluidic channel comprises an electrically charged wall, wherein the electrically charged wall is positively charged or negatively charged.

4. The device of claim 1 further comprising analyte substrates disposed within the rigid microfluidic channel, the analyte substrates at least partially obstructing flow through the rigid microfluidic channel and being consumable by at least one analyte, wherein the analyte substrates are embedded in a polymer structure, wherein the analysis is configured to relate flow rate through the microfluidic channel to concentration of the at least one analyte; wherein one or more porous polymer structures is disposed in the rigid microfluidic channel, the one or more porous polymer structures defining one or more pore sizes for separating or isolating different analytes; the device further comprising conductive material disposed in the rigid microfluidic channel and connected to the power source, and an aptamer, antibody, or combination of such in the rigid microfluidic channel.

5. The device of claim 4, wherein the aptamer, antibody, or combination of such are embedded directly into the rigid microfluidic channel, are embedded in the conductive material, or are disposed on a surface of the conductive material, the device further comprising a pair of electrodes spanning the rigid one microfluidic channel, wherein the microcontroller is configured to detect or measure binding of an analyte to the aptamer, antibody, or a combination using the pair of electrodes, and wherein the conductive material comprises a nanoparticle sheet, a polymer, a hydrogel, or a microgel.

6. The device of claim 1, wherein the microcontroller is configured to measure voltage, current, resistance, resistivity, conductivity, circuit frequency, time, electrical induction, capacitance, or a combination of such.

7. The device of claim 1, further comprising at least one further biosensor disposed on the substrate outside the rigid microfluidic channel, the at least one biosensor disposed on the substrate configured to detect or measure the fluid and the at least one analyte surrounding the substrate.

8. The device of claim 1, wherein at least one biosensor comprises an aptamer, antibody, or combination of such.

9. The device of claim 1, further comprising an adhesive layer at a surface of the substrate, the adhesive layer configured to adhere the substrate to a carrier, wherein the adhesive layer comprises a bioadhesive configured to adhere to internal tissue of the patient, wherein the carrier is a medical device or a surgical instrument.

10. The device of claim 1, wherein the at least one biosensor is configured for electrolytic voltammetric fluid detection.

11. The device of claim 1, wherein the power source comprises a battery.

12. The device of claim 1, wherein the power source comprises an inductive coil for receiving power from a remote device outside the body.

13. The device of claim 1, wherein the wireless communications interface comprises a radio-frequency identification device.

14. The device of claim 1, wherein the remote device comprises a transdermal patch, a smartphone, a tablet computer, or a computer.

15. The device of claim 1, wherein the wireless communications interface includes rigid antenna and is configured to wirelessly communicate data through body tissue to the remote device.

16. The device of claim 1, wherein remote device includes a user interface to display analysis data received from the wireless communications interface.

17. The device of claim 1, wherein the rigid microfluidic channel further comprise an outer membrane positioned to cover the open end of the rigid microfluidic channel, the outer membrane configured to be selectively openable to controllably allow the passage of biological fluids.

18. The device of claim 17, wherein when the outer membrane is in an open position, the outer membrane allows fluid to flow through the length of the rigid microfluidic channel, and wherein the at least one biosensor disposed in the rigid microfluidic channel is configured to analyze the flowing fluid upon entry of the fluid to the rigid microfluidic channel.

19. The device of claim 1, wherein the at least one biosensor contained in the rigid microfluidic channel is configured to measure flow rate of the fluid that contains the at least one analyte.

20. A system for detecting postoperative complications in a patient, the system comprising:
 a transdermal patch configured to adhere to skin of a patient, the transdermal patch including a wireless communications interface;
 a substrate made of biocompatible or biodegradable material;
 at least one biosensor disposed at the substrate, the at least one biosensor configured to detect or measure at least one analyte in a body of the patient;
 a rigid microfluidic channel defined by the substrate, the rigid microfluidic channel comprising a passage for a fluid, the rigid microfluidic channel containing the at least one biosensor therein, the fluid comprising the at least one analyte;
 a wireless communications interface disposed on the substrate;
 a microcontroller disposed on the substrate, the microcontroller connected to the at least one biosensor and the wireless communications interface, the microcontroller configured to measure at least one signal from the at least one biosensor and transmit measured data through the wireless communications interface disposed on the substrate to the wireless communications interface of the transdermal patch; and
 a power source disposed on the substrate for powering the wireless communications interface disposed on the substrate and the microcontroller.

21. The system of claim 20, wherein the transdermal patch further comprises a processor configured to perform an analysis on the measured data.

* * * * *